United States Patent
Chen et al.

(10) Patent No.: US 7,309,467 B2
(45) Date of Patent: Dec. 18, 2007

(54) FLUIDIC MEMS DEVICE

(75) Inventors: Chien-Hua Chen, Corvallis, OR (US); Xia feng Yang, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 749 days.

(21) Appl. No.: 10/606,023

(22) Filed: Jun. 24, 2003

(65) Prior Publication Data

US 2004/0265182 A1    Dec. 30, 2004

(51) Int. Cl.
*B01L 3/02* (2006.01)
*B01L 11/00* (2006.01)
*B32B 5/02* (2006.01)
*B32B 27/04* (2006.01)
*B32B 27/12* (2006.01)

(52) U.S. Cl. .............. 422/100; 422/50; 422/68.1; 422/81; 422/82; 422/101; 422/102; 422/103; 436/43; 436/52; 436/53; 436/174; 436/177; 436/180

(58) Field of Classification Search ........... 422/50, 422/68.1, 81, 82, 100–103; 436/43, 52, 53, 436/174, 177, 180
See application file for complete search history.

(56) References Cited

U.S. PATENT DOCUMENTS 5,375,979 A    12/1994  Trah

| 2002/0098097 A1 | 7/2002 | Singh |
| 2002/0117517 A1 | 8/2002 | Unger |
| 2003/0007715 A1 | 1/2003 | Loock |
| 2003/0017467 A1 | 1/2003 | Hooper |

FOREIGN PATENT DOCUMENTS

| EP | 1 283 563 | 2/2003 |
| WO | WO 98/45693 | 10/1998 |
| WO | WO 01/38844 | 5/2001 |
| WO | WO 01/96958 | 12/2001 |
| WO | WO 02/43615 | 6/2002 |

OTHER PUBLICATIONS

J.H.Daniel, "Silicon microchambers for DNA amplification", Sensors and Actuators vol. 71, No. 1-2, Nov. 1, 1998, pp. 81-88.

*Primary Examiner*—Brian Sines

(57) ABSTRACT

A fluidic micro electro-mechanical system (MEMS) device is described. In one aspect, at least one at least partially covered fluidic channel is formed between a polymer layer and a polymer substrate as the polymer layer is deposited on the substrate. The partially covered fluidic channel is fabricated as a unitary polymer layer structure. In one implementation, a strong exposure process is applied to the polymer layer to create a deep cross-linked polymer region. A weak exposure process is applied to the polymer layer to create a shallow cross-linked polymer region.

13 Claims, 19 Drawing Sheets

FLUIDIC MEMS DEVICE

TECHNICAL FIELD

This invention relates to Micro Electro-Mechanical Systems (MEMS), and more particularly to MEMS that can contain or transport fluids.

BACKGROUND

Many types of Micro Electro-Mechanical Systems (MEMS) provide electrical sensing, controls, and calculation. MEMS technology is being applied to continually smaller systems, and recently has been applied to nano-scale systems. Designing for continually smaller devices, particularly down to and into the nano-scale dimensions, provides considerable design challenges.

Considerable complexity results when MEMS devices and circuits are applied to hostile environments. One of the most challenging environments that MEMS, or any electronic circuit, can be designed for, or applied to is fluids (and more particularly blood, other bodily fluids, or difficult to handle fluids). MEMS can be configured to sense or monitor a variety of parameters within the human body as well as in many other applications. The electronic device has to be protected from such hostile environments to provide an accurate measurement of the fluid.

One prior art embodiment of a MEMS device 29, as illustrated in FIG. 1, can be integrated within certain chemical analysis systems. The MEMS device 29 includes a plurality of substrates 34 and 36. Grooves and/or channels 28 are etched into one or both of the respective etched faces 30, 32 of the two respective substrates 34, 36. The etched faces of each one of the two substrates are bonded together at a bonded region 38 as illustrated in FIG. 2 such that they are positioned to face each other. Since the etched faces are mounted to face each other, a pair of etched grooves (i.e., one groove in each of the etched faces) can together form a conduit surrounded on each side by one of the substrates.

The substrates 34, 36 can be manufactured from a glass (such as Pyrex®—a trademark of Corning) or a semiconductor such as silicon. The substrates are bonded together so the etched channels and/or grooves 28 (as shown in FIG. 1) in one or both of the etched faces 30, 32 of the substrates form a conduit that provides fluidic communications. The substrates can be bonded using anodic bonding technique or with glass frit intermediate layers. The conduits that provide fluidic communications include fluidic I/O ports as well as the fluidic channels.

Such prior art techniques can use known fabrication to create the etched channels and/or grooves 28 as shown in FIG. 1 having a desired dimension down to, and including, tens of nanometers. However, aligning the etched channels and/or grooves 28 on pairs of bonded substrates takes a considerable amount of time and effort. As such, it is difficult to use such matched substrate configurations in large scale production. In addition, such bonded substrate pairs are costly to produce.

BRIEF DESCRIPTION OF THE DRAWINGS

The same numbers are used throughout the drawings to reference similar features and components.

DETAILED DESCRIPTION

A fluidic micro electro-mechanical system (MEMS) device 200 is a MEMS device that is capable of conveying, holding, and/or interfacing with fluids. This disclosure provides a variety of embodiments of fluidic MEMS devices 200. This disclosure provides a mechanism by which fluidic MEMS devices can be produced reliably, cost efficiently, and using few parts that have to be connected. One exemplary application of MEMS devices involves transporting/monitoring human or animal fluids such as blood. Packaging of fluidic MEMS devices 200 can be very challenging considering that the devices sometimes have to effectively interface with the outside world, distribute fluid within the MEMS, and interact with fluid. Examples of such fluidic MEMS devices 200 include chemical analysis systems and microarrays. One embodiment of a collection of micro-scale chemical and biological analysis systems all located on the same chip provides a "lab-on-a-chip" design.

In one aspect, fluidic MEMS devices 200 can be created by using a direct imaging process. One embodiment of the direct imaging process includes a photosensitive polymer such as Su8 (the use of Su8 is generally known in the semiconductor industry and is commercially available).

A large variety of embodiments of the fluidic MEMS device 200 can be produced that include, but are not limited to, a fluidic channel, a fluid pump, a fluid filter, a material separator (using electrophoresis), a chemical detector, a reactor, and a fluid connector. In addition, this disclosure describes multiple embodiments of fabricating a variety of such MEMS devices in an interconnected fashion.

Figure 4:
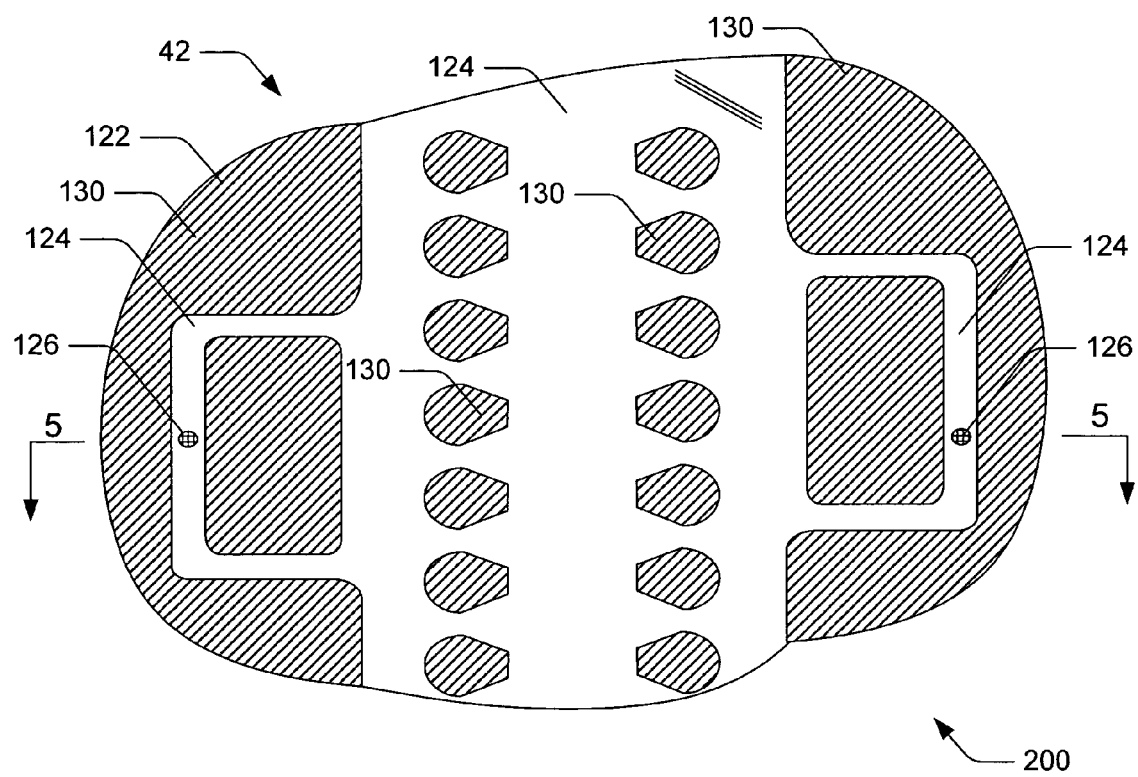
FIG. 4 illustrates a top view of one embodiment of a fluidic micro electro-mechanical system (MEMS) that is fabricated using polymer layer technique.
Figure 5:
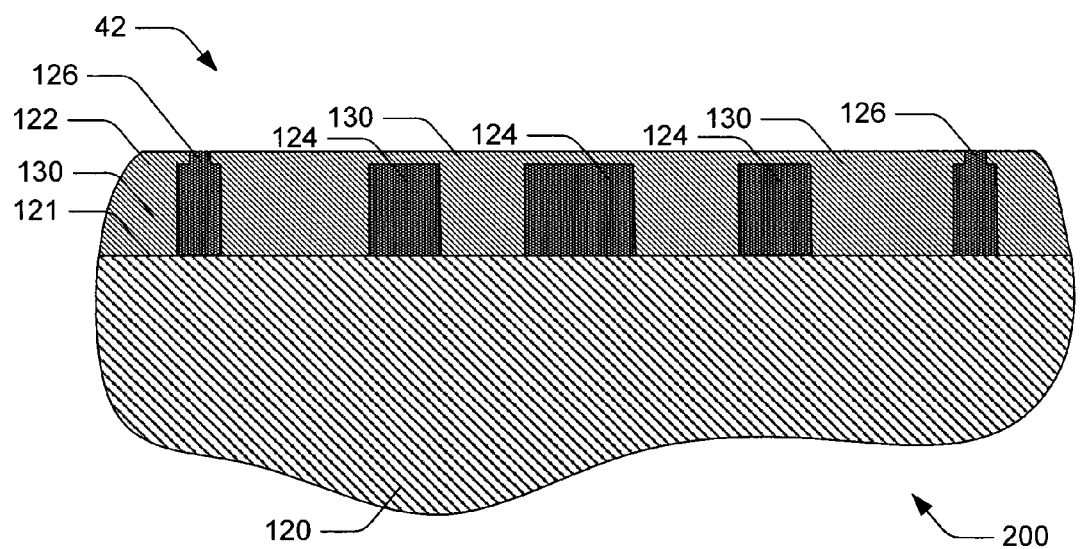
FIG. 5 illustrates a side sectional view as taken through cross-sectional lines 5-5 of FIG. 4.

One aspect of fluidic MEMS devices 200 relates to creating one or more fluidic channels 124 that convey fluids between the different components within each fluidic MEMS device 200. The fluidic channels 124 may be configured to be quite narrow in depth (e.g., in certain embodiments, less than 100 nanometers). An assembled system including a variety of fluidic MEMS devices 200 can be produced using a polymer layer structure 42 as shown in FIGS. 4 and 5 that includes a polymer material, as illustrated in block form in FIG. 3. The unitary polymer layer structure 42 can be fabricated as described relative to FIGS. 6a, 6b, 6c, 6d, and 6e using a technique described in FIG. 7.

Certain embodiments of the fluidic MEMS device 200 can be configured to include a filter structure. In another embodiment, the fluidic MEMS device 200 can provide a reaction chamber (e.g., an integrated planar polymerase chain reaction (PCR) chamber).

Figure 3:
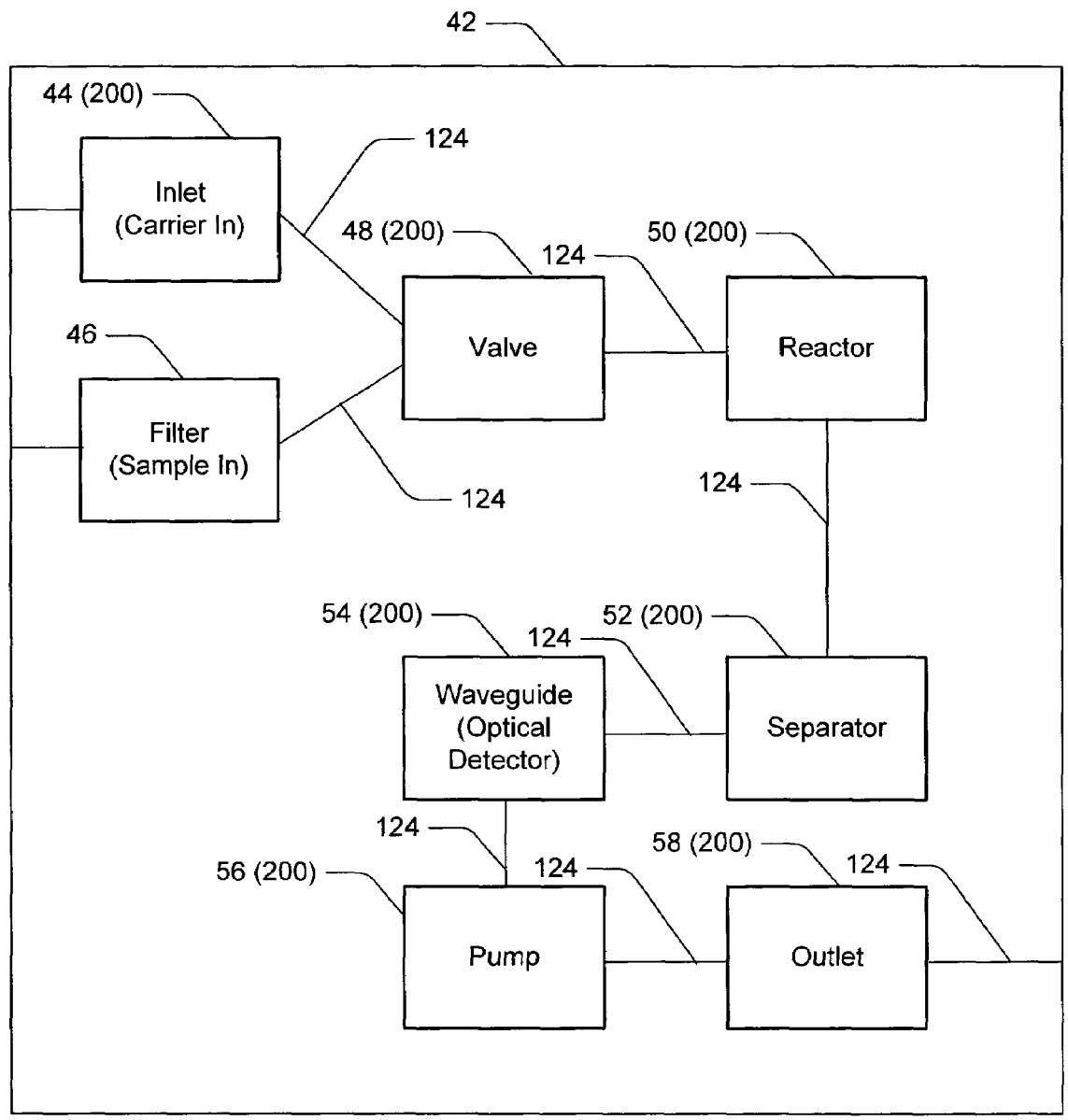
FIG. 3 illustrates one embodiment of a chemical analysis system that is fabricated using one embodiment of polymer layer technique.

FIG. 3 illustrates a top view of one embodiment of a plurality of fluidic MEMS devices 200 arranged on a unitary polymer layer structure 42. The unitary polymer layer structure 42 includes a variety of devices that are formed either entirely in the polymer layer, or alternatively in the polymer layer and the upper surface of the substrate. One embodiment of the unitary polymer layer structure 42, as shown in FIG. 3, includes (as fluidic MEMS devices 200) an inlet 44, a filter 46, a valve 48, a reactor (heater) 50, a separator 52, a waveguide 54 for optically detecting, a pump 56, and an outlet 58. A plurality of fluidic channels 124 connect the different fluidic MEMS devices 200 shown in FIG. 3. The filter 46 acts to filter out items that have at least one dimension that is larger than a prescribed dimension. The waveguide 54 transmits the concentration information relating to concentrations of one or more chemicals in a sample, such as a liquid. The valve 48 selects that fluid (which is supplied from the inlet 44 and/or the filter 46) that will be input to the reactor 50. The reactor 50 includes a fluid channel that in one version is arranged in a serpentine configuration to increase the length of the fluid channel of the reactor to enhance heat transfer.

In one version, a plurality of heating elements (each heating element having a different heating area) are disposed proximate the heating channel. The heating elements having different heating areas can be selectively and individually actuated to heat the fluid traversing to fluid element to different heating temperatures at different times to effectively perform the PCR process. It is generally known in the PCR process to heat the fluid to different temperature levels at different times. In an alternate embodiment, the amount of electrical current traversing a single (or more than one) heating element can be varied to apply different heating levels to the fluid traversing the fluid element to different temperatures to perform the PCR process.

The separator separates different components from a sample based on electric charge applied to the different components of the sample. Different components are displaced by different lengths along the channel based on the properties of the different components. Fluidic channels 124 connect between certain ones of the devices 44, 46, 48, 50, 52, 54, 56, and 58 as illustrated in FIG. 3, and each fluidic channel 124 provides the only fluidic path between the particular devices as illustrated. Substantially all of the fluid that enters a fluidic channel 124 either remains within the channel or exits the channel.

The particular devices 44, 46, 48, 50, 52, 54, 56, and 58 that are illustrated in FIG. 3 are illustrative in nature and are not limiting in scope, since any combination of devices that are produced using the unitary polymer layer technique as described herein is within the intended scope of the present disclosure.

A number of techniques that can be useful in biological or chemical analysis systems include, but are not limited to, electrophoresis, free-flow electrophoresis, electrical field-flow fractionation (EFFF), polymerase chain reaction (PCR), gas chromatography, liquid chromatography, and hybrid systems. The fluidic MEMS device 200 can be applied to many of these techniques.

Using techniques described relative to the embodiment of unitary polymer layer structure 42, a plurality of fluidic MEMS devices 200 are fabricated on a single chip that, in certain embodiments, is configured to provide chemical or biological analysis using an integrated waveguide. An integrated total chemical analysis system can therefore be produced by using a direct imaging process. Many prior art systems rely on a wafer bonding process. One embodiment of the chemical or biological analysis system incorporates a focus lens and a mechanical fiber alignment guide.

Figure 1:
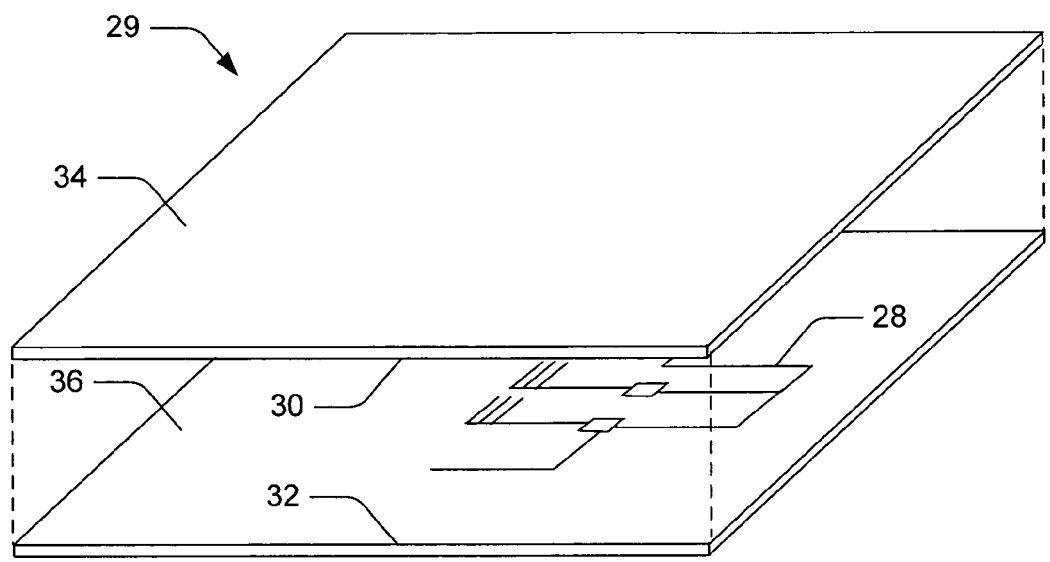
FIG. 1 illustrates a prior art wafer bonding process in which a plurality of wafers are being spaced in a position to be moved toward each other and be bonded to each other.
Figure 2:
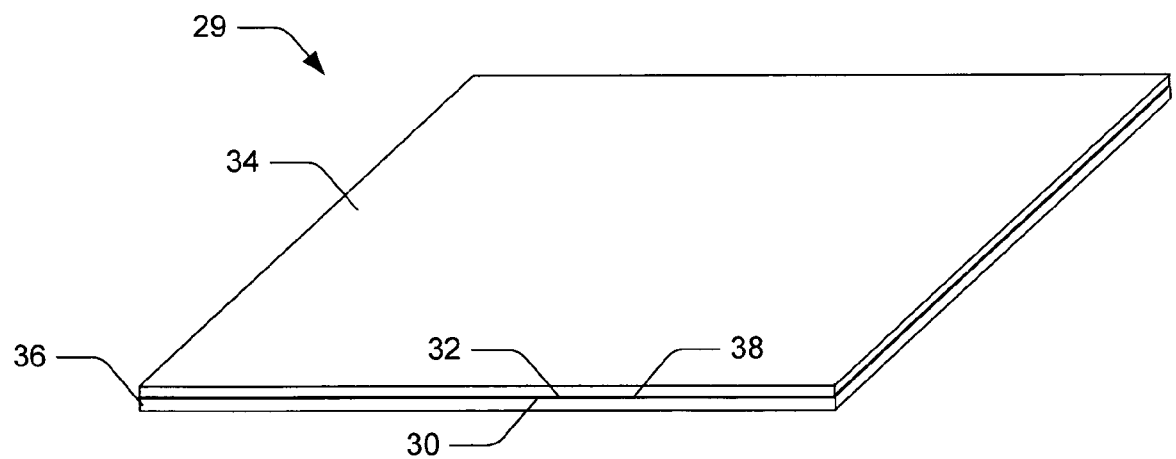
FIG. 2 illustrates the prior art bonding process of FIG. 1 in which the plurality of wafers are bonded together.

A common prior art technique to package MEMS, as described in the Background portion of this disclosure relative to FIG. 1, is to etch grooves and/or channels 28 into the faces 30, 32 formed on a pair of silicon or Pyrex® (a trademark of Corning) glass substrates 34, 36. The substrates 34, 36 are bonded together to create the bonded region 38 as shown in FIG. 2 such that the grooves and channels 28 in the etched faces 30, 32 form fluidic I/O ports as well as fluidic channels between components. An anodic bonding technique (or use of glass frit intermediate layers) can bond the region 38 in the microfabricated chip.

When each one of the multiple faces 30, 32 are etched, the respective substrates 34, 36 are aligned as shown in the prior-art configuration of FIGS. 1 and 2 in such a manner that the grooves and/or channels on one substrate 34 are aligned with the grooves and/or channels on another substrate 36. If a number of bonded regions are to be fabricated (e.g., to form a multi-layered structure), then the process of aligning and bonding successive pairs of bonded substrates that is performed at each successive bonded region 38 is repeated for each subsequent substrate.

As shown in FIG. 3, the present disclosure provides a mechanism by which a variety of fluidic MEMS devices 200 can be fabricated as a unitary polymer layer structure 42 formed within a polymer layer located on a substrate 120. The fluidic channels 124 thereby form the vehicle through which fluid passing between sets of fluidic MEMS devices 200 can be conveyed. Other non-channel fluidic MEMS device 200 (e.g., fluid pump, fluid filter, fluid reactor) can be considered as integrating a fluidic channel 124 that encases the fluid, and directs the fluid to flow through the functional components of the device itself.

The fluidic MEMS device can be fabricated as a unitary polymer layer structure 42, as described herein. FIGS. 4 and 5 illustrate one embodiment of the unitary polymer layer structure 42. As shown in FIG. 5, the unitary polymer layer structure 42 (using an exposure/developing process as described in this disclosure) is secured to the substrate 120. For direct imaging, two exposure processes are used: weak and strong. The unitary polymer layer structure 42 forms with the substrate 120 one or more fluidic channels 124 connecting one of more fluidic MEMS device 200. The unexposed material is then developed away, and thereby removed. Recesses are often formed in the polymer material forming the polymer layer to allow the unexposed material to be removed (many of which are plugged after the direct imaging process to create fluid-tight fluidic channels). The location of the developed away unexposed material typically corresponds to the fluidic channels 124. The polymer material is then cured using heat and/or ultra-violet (UV) light exposure. The curing process is generally known with each particular polymer, differs somewhat between different polymers, and will not be further described herein.

In one embodiment, the polymer material of which the unitary polymer layer structure is formed includes a fast cross-linking polymer such as photoimagable epoxy (such as SU8 that is commercially available), a photoimagable polymer, or a photosensitive silicone dielectrics (such as SINR-3010 manufactured by ShinEtsu™).

Certain fluidic channels 124 are in communication with a through-hole 126 by which fluid can be introduced into, or out of, the fluidic channels 124 from above (the directions taken as per FIG. 4) the polymer structure region 122. The combination of the fluidic channels 124 and the through-holes 126 together form a pattern described herein as partially covered channels 124 (the term "partially" relates to the possibility of providing openings in any covering for the through-holes 126).

The unitary polymer layer structure 42 includes a fluidic containment material 130. The fluidic containment material 130 is joined with the substrate 120 at junctions 121 to form the fluidic channels 124 in a manner to direct fluid within the prescribed fluidic channels 124 (and providing the through-holes 126 as one route of escape from the fluidic channels) along the intended route for the fluid. The fluidic containment material 130, the fluidic channels 124, and the through-holes 126, therefore combine to form the polymer layer structure 42 on top of the substrate 120 as illustrated in FIG. 5. In one embodiment, the fluidic channels 124 therefore are formed as an interface between the unitary polymer layer structure 42 and the substrate 120. The portion of the unitary polymer layer structure 42 that is used to fabricate the fluidic containment material 130, the fluidic channels 124, and the through-holes 126 can thereby be fabricated as a unitary structure in certain embodiments.

The unitary polymer layer structure 42 described in this disclosure reduces the expense, time, and effort associated with micromachining MEMS devices within one or two glass substrates (as with the prior art wafer bonding process), and then bonding the two substrates together to form the desired channel configuration. Certain embodiments of the fluidic MEMS devices 200 can be produced relatively easily, and therefore the associated production cost is reduced. The fabrication techniques associated with producing many fluidic MEMS components are also simplified and enhanced.

In one embodiment, the polymer layer structure 42 is formed as a unitary member that attaches to the substrate to create the fluidic MEMS devices 200. Therefore, certain portions (including, but not necessarily limited to, one or more of the fluidic containment material 130, the fluidic channels 124, and the through-holes 126) are formed as a unitary polymer layer structure 42 with the substrate 120 as described in this disclosure. The use of the unitary polymer layer structure 42 provides several advantages.

With the prior art embodiment of rigid attached substrates 32, 34 as shown in FIGS. 1 and 2, it is more difficult to seal the individual channels. Namely, it is typically more difficult to form a secure channel using the channels 28 in the two rigid substrate plate members 34, 36 shown in the prior-art system of FIGS. 1 and 2 than it is to form a secure channel between the unitary polymer layer structure 42 and the substrate 120 as shown in FIG. 5 using the techniques described herein. This concept applies even to such relatively small scaled devices as nano-scale, meso-scale, macro-scale, and micro-scale fluidic MEMS devices 200.

Additionally, the unitary polymer layer structure 42 ensures an improved sealing effectiveness compared to connected composite members. Such improved sealing effectiveness translates into increased useful lifetimes, improved operation, and improved sensitivity for fluidic MEM devices. Additionally, by forming the grooves and/or substrates on a single substrate as is the case with certain embodiments of the unitary polymer layer structure 42, multiple substrates do not have to be aligned to form a fluidic conduit. Such alignment processes generally can be expensive, laborious, and error prone.

The fluidic MEMS devices 200 as described herein can be packaged without using alignment techniques between a plurality of substrates 34 and 36 (the alignment is described relative to the prior art structure shown in FIGS. 1 and 2). The fabrication of the unitary polymer layer structure 42 on a single layer of substrate relies on a polymer material and direct imaging process. A wide variety of fluidic MEMS devices can be fabricated using the unitary polymer layer technique as described in this disclosure.

The unitary polymer layer structure 42 can be referred, due to its shape, as a top-hat structure considering the configuration shown in FIG. 5. The different portions of the fluidic MEMS devices having different vertical depths as shown in FIG. 5, can be fabricated using different strength direct imaging processing techniques. The top-hat structure not only provides protection to the unitary fluidic MEMS device 200 but also creates built-in fluidic channels 124 for fluid delivery. The polymer material can provide an I/O port for unitary fluidic MEMS to communicate with the outside world. This new technology can significantly reduce the cost of packaging of unitary MEMS and enhance the functionality of the different embodiments of the fluidic MEMS device 200.

The unitary polymer layer technique provides a variety of fluidic MEMS devices 200. An enclosed cavity can be created within certain fluidic MEMS devices formed on one side by the substrate and on another side by the polymer layer. The polymer layer is formed as a unitary structure to reduce the possibility of fluid leakage, contamination, etc. that may occur by the contents within the enclosed cavity mixing with the contents external of the polymer layer. In one embodiment, the fluidic MEMS device is capable of a fully integrated total chemical analysis or other fluidic MEMS devices 200 (and/or components) with significantly reduced cost and/or reliability.

Instead of wafer bonding, the unitary polymer layer technique described herein proposes that the unitary fluidic MEMS devices 200 can be largely enclosed between the polymer material (such as SU8) of the unitary polymer layer structure 42 and the substrate 120 using direct imaging processing techniques. The top-hat structure not only provides protection to, and integrity between, individual fluidic MEMS devices 200 (and components thereof) but also creates built-in fluidic cavities and/or fluidic channels 124 for fluid delivery that may be secured using glue/epoxy as described in this disclosure. The polymer material can also be patterned to create an interface port to the outside world. This new technology can significantly reduce the cost of packaging and enhance the functionality of the fluidic MEMS devices 200.

The unitary polymer layer structure 42 as illustrated in FIGS. 4 and 5 can be fabricated using a direct imaging process as described relative to FIGS. 6a, 6b, 6c, 6d, 6e, and 7. This disclosure indicates that a wide variety of fluidic MEMS devices 200 can be packaged using a polymer material (such as SU8) using the direct imaging process. The top-hat structure provided by the unitary polymer layer technique not only provides protection to the fluidic MEMS device 200 but also provides for built-in fluidic channels 124 to provide fluid delivery. The polymer material can also be patterned with through-holes 126 to create an interface port to outside the fluidic MEMS device.

Direct imaging process can be used to generate top-hat structures from polymer that are capable of improving the sealing of built-in fluidic channels 124 that are contained within fluidic MEMS devices 200 as well as fluidic conduits. The top-hat structure also provides a more secure structure to secure fluidic MEMS devices relative to the fluidic conduits. FIGS. 4 and 5 illustrate, respectively, a top-down view and a cross-section view of an exemplary fluidic MEMS device structure that is created using a direct imaging process. SU8 resist is applied to a wafer or substrate 120 followed by an appropriate number of exposures to create the through-hole 126, the fluidic channel 124, and the top-hat structure.

The direct imaging process allows for the creation of built-in fluidic channels 124 formed including a unitary polymer layer that connects various components or cells. The direct imaging process generally includes the spin-coat deposition of a thick SU8 material. Different embodiments of the SU8 material are typically between 2 and 200 µm (even though the material may be fabricated outside of these dimensions). Multiple direct imaging exposure processes can be formed using a plurality of top-hat and chamber masks and a related cross-linking process. This direct imaging process creates a varied configuration of the fluidic channel 124 and top-hat structures. In addition to fluidic channels 124, various fluidic MEMS devices 200 can be produced using the direct imaging process as described herein.

Figure 6A:
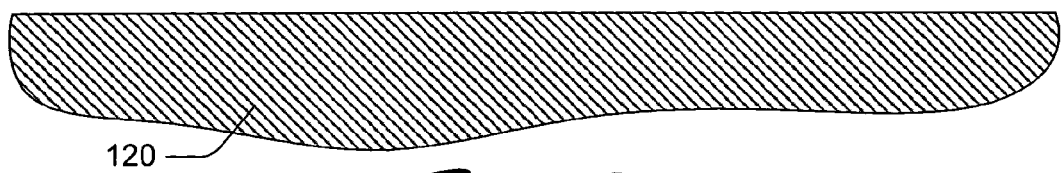
FIGS. 6a, 6b, 6c, 6d, and 6e illustrate side cross sectional views of one embodiment of the fluidic MEMS device (in this instance a fluidic channel) during fabrication.
Figure 6B:
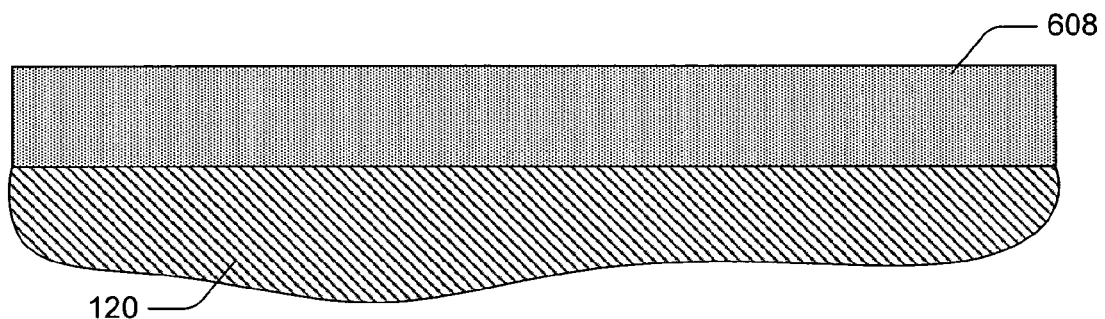
Figure 6C:
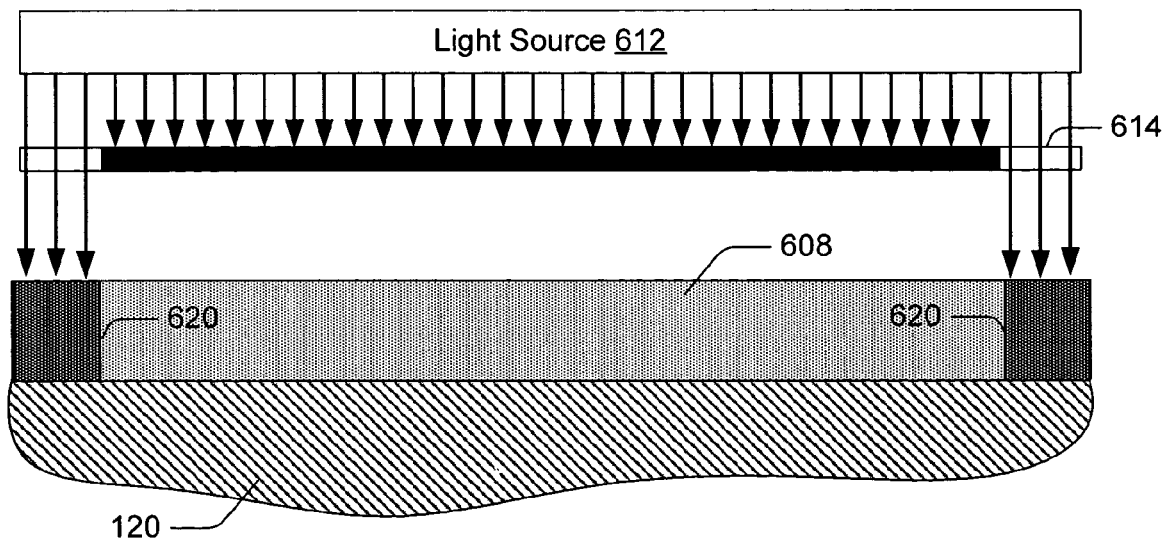
Figure 6D:
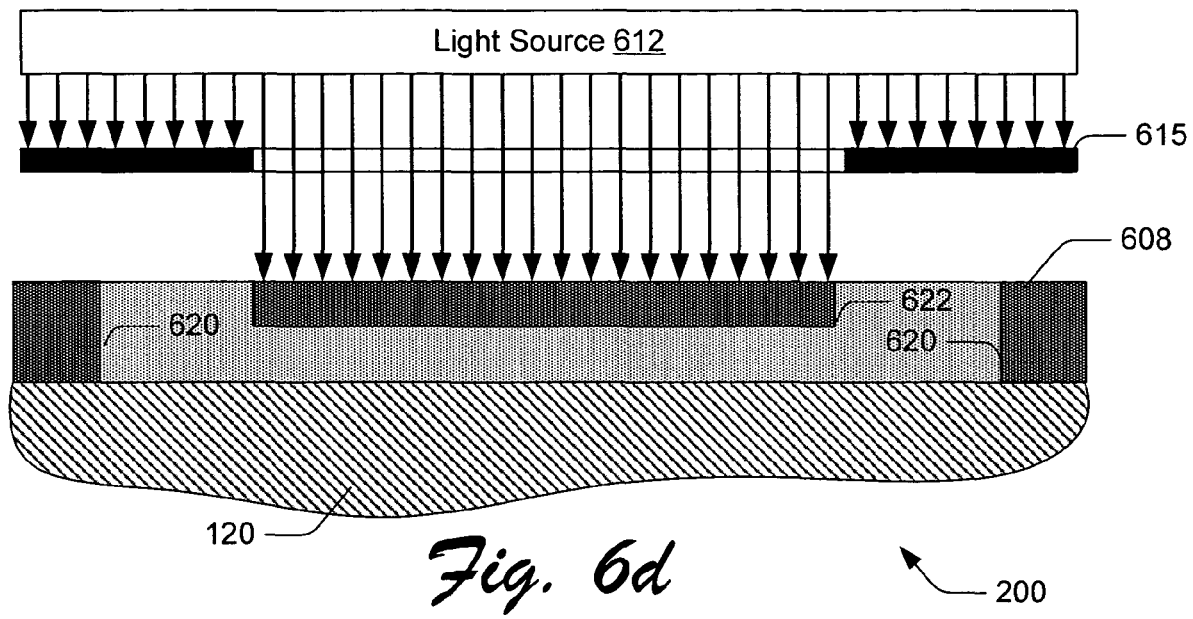
Figure 6E:
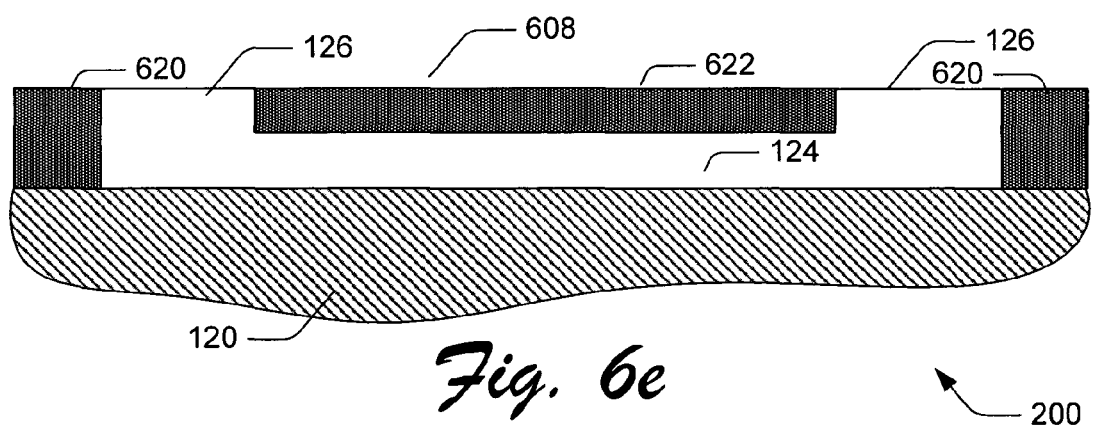
Figure 7:
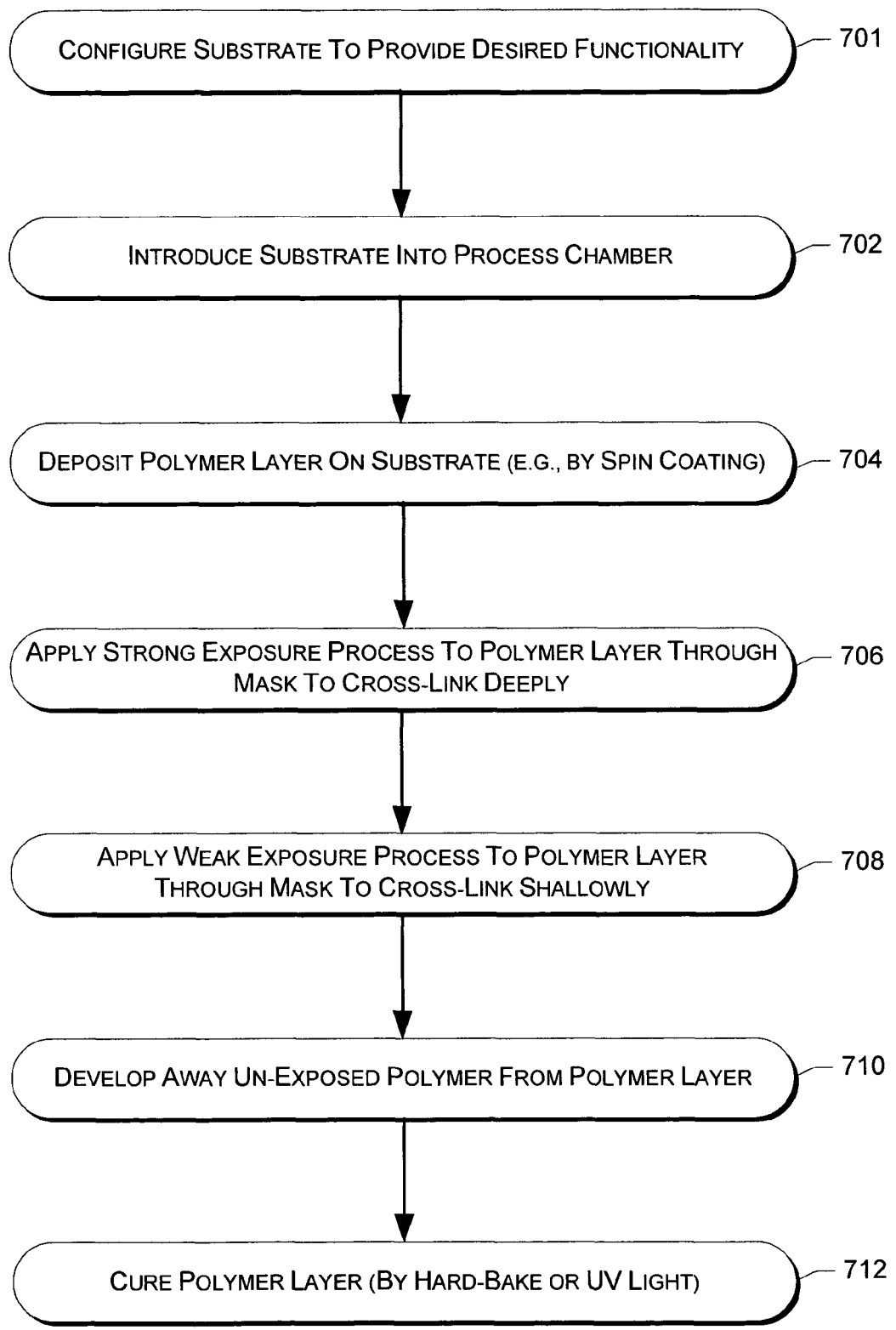
FIG. 7 illustrates a direct imaging cross-linking process that is used to fabricate a fluidic MEMS (such as the embodiment illustrated in FIGS. 6a, 6b, 6c, 6d, and 6e) using the controller/computer as illustrated in FIG. 25.

FIGS. 6a, 6b, 6c, 6d, and 6e illustrate one embodiment of fluidic MEMS device 200 being fabricated on a substrate 120 using a direct imaging process 700 as indicated on FIG. 7. In FIGS. 6a, 6b, 6c, 6d, and 6e, the fluidic MEMS device 200 being fabricated is a fluidic channel 124, many of which are shown in block diagram form in FIG. 3. The fluidic channel 124 conveys fluid from one location to another. Each fluidic MEMS device 200 as described herein integrates a fluidic channel portion since the flow of fluid typically has to be controlled as the fluid flows through the fluidic MEMS device 200 (even as the fluid is undergoing the operation of each particular fluidic MEMS device). The general fabrication techniques described relative to FIGS. 6a, 6b, 6c, 6d, and 6e relate to different embodiments of the fluidic MEMS device 200.

A variety of embodiments of the fluidic MEMS devices 200 that can be fabricated using the direct imaging process 700 as described relative to FIG. 7. Certain illustrative and non-limiting ones of these embodiments are described. One embodiment of the direct imaging process 700 as described relative to FIG. 7 may be performed using an embodiment of a computer/controller 800 that controls a process portion 802 as described relative to FIG. 25. The process portion 802 may be, for example, one or more fabrication chambers or process chambers that can perform a variety of processes on a substrate. The direct imaging process 700 as described relative to FIG. 7 includes 701 in which the substrate is configured as desired prior to processing. The configuration of the substrate depends largely on the intended function of the fluidic MEM device 200. For instance, if the fluidic MEM device 200 has a heating or electric conductor function, then the substrate can be respectively provided with a heating element or an electrical conductor.

Alternatively, an electrical, optical, or electromechanical sensor can be provided as another embodiment of the fluidic MEMS device 200. If the substrate of the fluidic MEM device 200 is configured with a specific etched or deposited region or other configuration (such as with an etched recessed portion 752 as shown in its etched state in FIG. 8e), then the substrate is configured in 701. 701 occurs prior to the deposition of the polymer layer in 702, so that the substrate is configured as desired prior to the deposition of the polymer to be hardened by exposure and hard-bake during cross-linking.

In FIG. 6a, a substrate 120 (only a portion of which is illustrated) is introduced to one or more process chambers (not shown) as described in 702 of the direct imaging process 700 described relative to FIG. 7. In FIG. 6b, a polymer layer 608 is deposited on the substrate 120 as described in 704 of the direct imaging process 700. Any technique by which the polymer layer is deposited on a substrate can be used, such as by spin coating. The unitary polymer layer structure 42 as described relative to FIGS. 3, 4, and 5 is fabricated either entirely in the polymer layer 608, or alternatively is formed in the polymer layer above the junction with, and partially including, the substrate 120. One embodiment of the polymer layer 608 includes a photosensitive polymer (such as Su8 that is commercially available).

The polymer of the polymer layer 608 is capable of multiple (two, in one embodiment) levels of exposure and development in the cross-linking process as applied during a variety of direct imaging processes as described in this disclosure. The two masked direct imaging exposure processes are differentiated herein as a "strong direct imaging exposure process" 706 and a "weak direct imaging exposure process" 708. The polymer of the polymer layer can therefore be exposed by one or more light sources (e.g., that emits ultraviolet light designed for the particular polymer) having different intensities or durations that are referred to as the strong direct imaging exposure process 706 and the weak direct imaging exposure process 708. The strong direct imaging exposure process 706 causes the polymer, following exposure, to cross-link the polymer of the polymer layer to a deeper depth than the weak direct imaging exposure process 708. In one embodiment, the strong direct imaging exposure process 706 causes the entire depth of the polymer layer to be cross-linked. The weak direct imaging exposure process causes less than the entire depth be cross-linked. As such, the polymer layer can be selectively exposed to different vertical depths as a function of the exposure intensity and/or the exposure duration.

In one embodiment, the polymer of the polymer layer 608 typically undergoes two masked direct imaging exposure processes during the direct imaging process 700 as shown in FIG. 7. The strong direct imaging exposure process 706, as illustrated in FIG. 6c, is able to cross-link the polymer through, or nearly through, the entire depth of the polymer layer 608. The "weak direct imaging exposure process" (as illustrated in FIG. 6d) is capable of cross-linking the polymer only through some of the depth of the polymer layer 608.

Certain embodiments of the direct imaging process 700 use a combination of the strong direct imaging exposure process 706 and the weak direct imaging exposure process 708 to provide the polymer layer structure 42 in the polymer layer 608 in a variety of cross-sectional configurations. As such, the polymer layer 608 is selected to be able to respond suitably to both the strong direct imaging exposure process 706 and the weak direct imaging exposure process 708.

FIG. 6c illustrates one embodiment of the strong direct imaging exposure process 706 in which a light source 612 (which, in one embodiment, is an ultra-violet light source) directs sufficient photonic energy through a mask 614 into the polymer of the polymer layer 608. The strong direct imaging exposure process 706 produces (following cross-linking) one or more deeply cross-linked polymer regions 620 that correspond to the outline of the mask 614. The strong direct imaging exposure process 706 may be considered as applying a relatively high dose of photonic energy that is sufficient to cure certain areas of the polymer layer 608 through substantially the entire depth of the polymer layer. The strong direct imaging exposure process 706 is illustrated in FIG. 6c of the direct imaging process 700. Each deep cross-linked polymer region 620 extends substantially fully through substantially the entire vertical height of the polymer region 608. At the base of the deep cross-linked polymer region 620, certain embodiments are secured to the substrate 120 while other embodiments are not secured to the substrate.

The particular configuration of certain embodiments of the deep cross-linked polymer regions 620, as shown in FIG. 6c, are configured to define the outer lateral boundaries (both length and width) of the fluidic channels 124. Two steps that produce the cross-linked polymer regions 620 and 622 (as described relative to FIGS. 6c and 6d) include exposure and developing. In FIG. 6c, which is exposure of the deep cross-linked polymer regions 620, the vertical entire depth of the polymer layer 608 is exposed (using a strong exposure process).

The strong exposure process changes the property of the polymer layer in these regions that are being exposed through the entire depth of the polymer layer. As such, a wider channel will be provided by spacing the deep cross-linked polymer regions 620 further apart. As such, many openings in the mask 614 as illustrated in FIG. 6c will determine the lateral boundaries of the path (in the vertical plane) of the fluidic channels 124. Alternatively, certain embodiments of deep cross-linked polymer regions 620 define structural components within the fluidic MEMS device, such as flapper blades in a fluid pump as illustrated in FIG. 8c.

FIG. 6d illustrates one embodiment of the weak direct imaging exposure process 708 (which is performed at a weaker exposure intensity and/or for a shorter duration than the strong direct imaging exposure process 706 as described relative to FIG. 6c). With the weak direct imaging exposure process 708, a light source 612 (which, in one embodiment, is an ultra-violet light source) directs sufficient photonic energy through a mask 615 into the polymer of the polymer layer 608 to produce relatively shallow cross-linked polymer regions 622 in certain selected regions of the polymer layer. By cross-linking, smaller polymer macro-molecules are combined into larger molecules having an increased molecular weight. Curing of the cross-linked molecules acts to harden these molecules and the polymer material itself. In this cured state, the hardened cross-linked molecules can be inserted into a solvent to develop away the non-hardened polymer regions. Cross-linking, curing, and developing away in general is known in the industry, and will not be further described in great detail in this disclosure. The configuration of the selected regions for the weak direct imaging exposure process 708 is based on the configuration of the mask 615.

The weak direct imaging exposure process 708 may be considered as a relatively low dose (compared to the higher dose of the strong direct imaging exposure process 706) of photonic energy that is sufficient to cure the polymer through only a fraction of the entire depth of the polymer layer. The weak direct imaging exposure process 708 as illustrated in FIG. 6d is described in 708 of the direct imaging process 700. The strong direct imaging exposure process 706 and the weak direct imaging exposure process 708 are configured to define as a unitary structure (in combination with an upper surface of the substrate 120) the fluidic channel 124. While the strong exposure process in 706 is performed prior to the weak exposure process 708 in the embodiment of the direct imaging process 700 shown in FIG. 7, the order of 706 relative to 708 is illustrative in nature and not limiting in scope.

Each shallow cross-linked polymer region 622 as shown in FIG. 6d extends through only a percentage of the vertical height of the original polymer region 608. The configuration of the shallow cross-linked polymer region 622 corresponds to the location of the upper horizontal boundary of the fluidic channel 124. As such, fluid traveling within the contained based on the polymer of the shallow cross-linked polymer regions 622. The outline of the shallow cross-linked polymer regions are determined by the configuration of the mask 615 as indicated in FIG. 6d. The through-holes 126 as shown in FIG. 6e are formed in the shallow cross-linked polymer regions.

FIG. 6e illustrates removing the un-cross-linked polymer material from the polymer layer 608. The removal of the un-cross-linked polymer material as shown in FIG. 6e provides the final outline of the fluidic MEMS device 200 (the fluidic channel 124 with through-holes 126 in the embodiment shown in FIG. 6e). 710 of the direct imaging process 700 involves the developing away of the unexposed polymer material during the cross-linking process in which developing solution is applied to the unexposed polymer material to wash the unexposed polymer material from the exposed polymer material. Following the developing away, the fluidic MEMS devices 200 (in their final form) are produced between the polymer layer and the substrate. The un-cross-linked polymer is removed during the developing process when the polymer layer 608 is inserted into developer solution.

For example, the portion of the polymer layer 608 that is un-cross-linked, and is therefore removed during 710 as shown in FIG. 7, corresponds to the fluidic channels 124 and/or the through-hole 126 as shown in FIGS. 4 and 5. The cross-linked polymer material is either cross-linked during the strong direct imaging exposure process 706 as shown in FIG. 6c or the weak direct imaging exposure process 708 as shown in FIG. 6d. The cross-linked polymer material therefore forms the boundaries along with an upper surface and the lateral surfaces of the substrate of the fluidic channels 124. The through-holes 126 are formed in a portion of the cross-linked polymer material. The particular thickness of the cross-linked polymer layer can be selected based on the desired application of the fluidic MEMS device, the design practice of the fabricator, and/or other design or regulatory constraints.

The polymer layer is then cured in 712. The curing of the polymer of the polymer layer can occur by hard-bake or by the application of ultra-violet (UV) light. The particulars of the curing differs depending on the polymer used, and will not be further detailed. Many commercially available polymers are provided with instructions relating to the curing process of the polymer.

The particulars of the strong direct imaging exposure process 706 to produce the deep cross-linked polymer regions 620 and the weak direct imaging exposure process 708 to produce the shallow cross-linked polymer regions 622 is not provided in greater detail herein. It is to be understood that a wide variety of polymer materials, substrate configurations, and polymer layer depths products have different requirements to produce satisfactory layers as described in this disclosure. This disclosure will therefore not go into detail about any particular polymer and/or polymer layer configuration. A wide variety of fluidic MEMS devices 200 can be fabricated in the polymer layer 608 using the strong direct imaging exposure process 706 and the weak direct imaging exposure process 708. Only an illustrative number of these fluidic MEMS devices 200 are described in this disclosure. It is envisioned that any unitary polymer layer structure 42 that is fabricated within the polymer layer is within the intended scope of the present disclosure.

Considering the configuration of the fluidic MEMS devices 200 as shown in FIG. 6e in addition to the configuration shown in FIGS. 4 and 5, the dimensions of the through-hole 126 can be designed to be relatively small. The through-holes 126 provide the only fluidic communication between the fluidic channels in the polymer layer and the outside of the fluidic MEMS device 200. In certain embodiments such as illustrated in FIG. 6e, the polymer layer 608 includes the unitary polymer layer structure 42 which integrates the fluidic MEMS devices 200.

FIGS. 8a, 8b, 8c, 8d, and 8e illustrate another embodiment of the fluidic MEMS device 200 being fabricated on a substrate 120. The fluidic MEMS device 200 as shown in FIGS. 8a, 8b, 8c, 8d, and 8e acts as a fluid pump 56 (illustrated in FIG. 3). Each one of FIGS. 8a, 8b, 8c, 8d, and 8e corresponds to the fabrication as described relative to respective FIGS. 6a, 6b, 6c, 6d, and 6e, except that micro-check valves 750 are also fabricated as a distinct deep cross-linked polymer regions 620 as shown in FIG. 8c.

In one aspect of the fluidic MEMS device 200, the MEMS pump includes a pair of micro-check valves 750 and a resistor 760. Though the resistor 760 is shown in FIG. 8c, it is envisioned that a piezoelectric device can be used in place of the resistor 760. In those versions that a piezoelectric device on a membrane is used, a fluidic pumping motion can be provided by controllably applying a voltage to the piezoelectric device, thereby causing the piezoelectric device to expand and contract depending upon the applied voltage. The integrated MEMS pump can be fabricated using the direct imaging process to produce the pair micro-check valves that retard or allow the flow of fluid through a channel of the MEMS pump. The resistor 760 is formed in or attached to the substrate 120 prior to the deposition of the polymer layer 608 such that an electric voltage can be applied across the resistor (from a controllable current source or voltage source, not shown) to apply heat to fluid passing through the MEMS pump. Selectively applying heat to the fluid passing through the MEMS pump can produce a pumping action as described in this disclosure. The resistor 760 can be pulsed by an electrical voltage to generate a bubble that can displace fluid in a manner that can be used for pumping. Such pumping by bubble generation involves a localize heating wherein the temperature of the fluid in general is maintained at a prescribed level. Creating these bubbles involves a localized application of heat that does not considerably affect the overall temperature of the fluid traversing the fluid MEMS device. The particular configuration of the resistor 760 is a design choice.

Figure 8A:
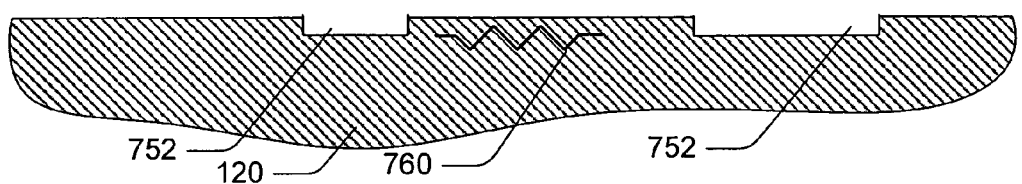
FIGS. 8a, 8b, 8c, 8d, and 8e illustrate side cross sectional views of one embodiment of a fluidic MEMS device (in this instance a pump) during fabrication.
Figure 8B:
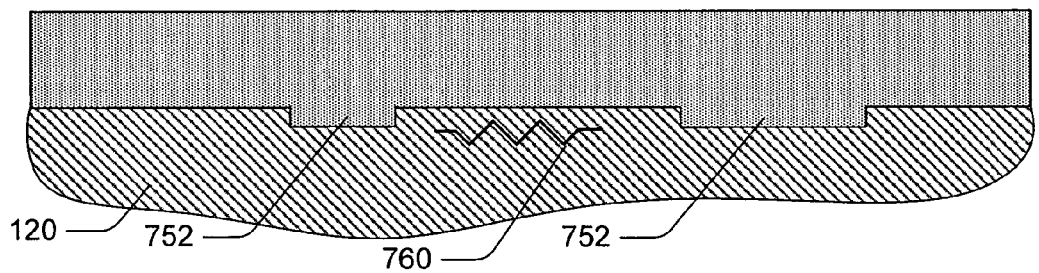
Figure 8C:
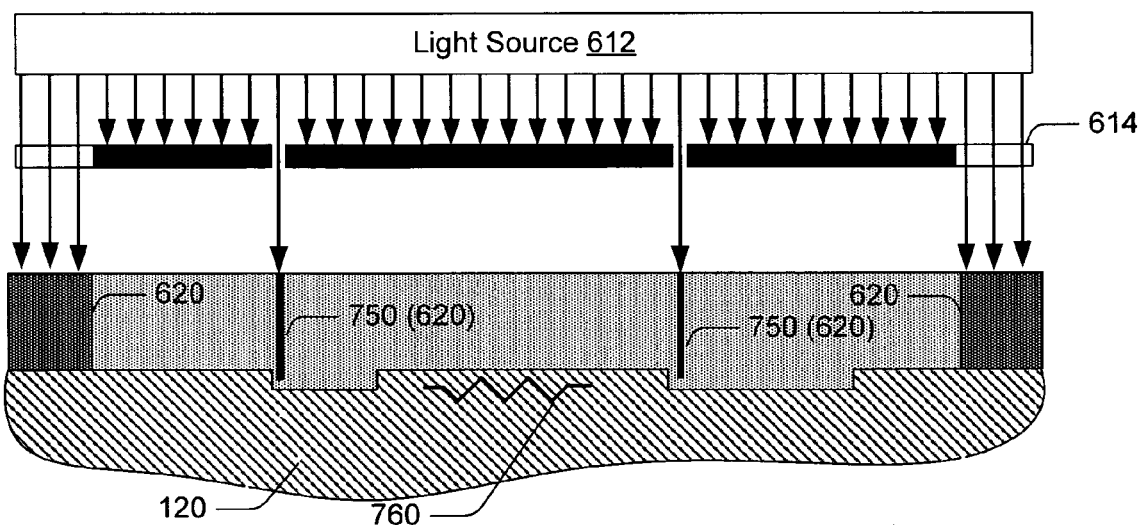

To provide the functionality of the micro-check valves 750, the substrate 120 illustrated in FIG. 8a includes one etched recessed portion 752 with which each respective micro-check valve 750 interfaces. The operation of the micro-check valve 750 in producing the pumping action is as described relative to FIGS. 9a, 9b, 9c, and 9d. The etched recessed portion 752 allows for lateral motion of the micro-check valves 750, while limiting excessive lateral motion of the micro-check valves 750. The micro-check valves 750 are configured to be sufficiently thin to provide the desired flexibility for the fluid pump 56 operation as illustrated in FIGS. 9a, 9b, 9c, and 9d while being sufficiently thick to provide the desired durability. Each micro-check valve 750 is configured to be freely-movable relative to the etched recess portion (the micro-check valve is not attached to the base of the etched recessed portion). As such, the polymer forming the micro-check valve 750 is not exposed to a level sufficient to cross-link the polymer layer all the way down to the etched recess portion 752. This can be accomplished by forming the etched recess portion to be sufficiently deep so the exposed portion of the polymer layer does not reach down to a base of the etched recess portion 752. Alternatively, the dosage of the exposure can be altered in the micro-checked valve to precisely control the exact height of each micro-check valve. These two techniques to ensure the micro-check valve 750 does not contact the etched recess portion to form a continuous unitary structure can be performed in combination, or separately.

Figure 8D:
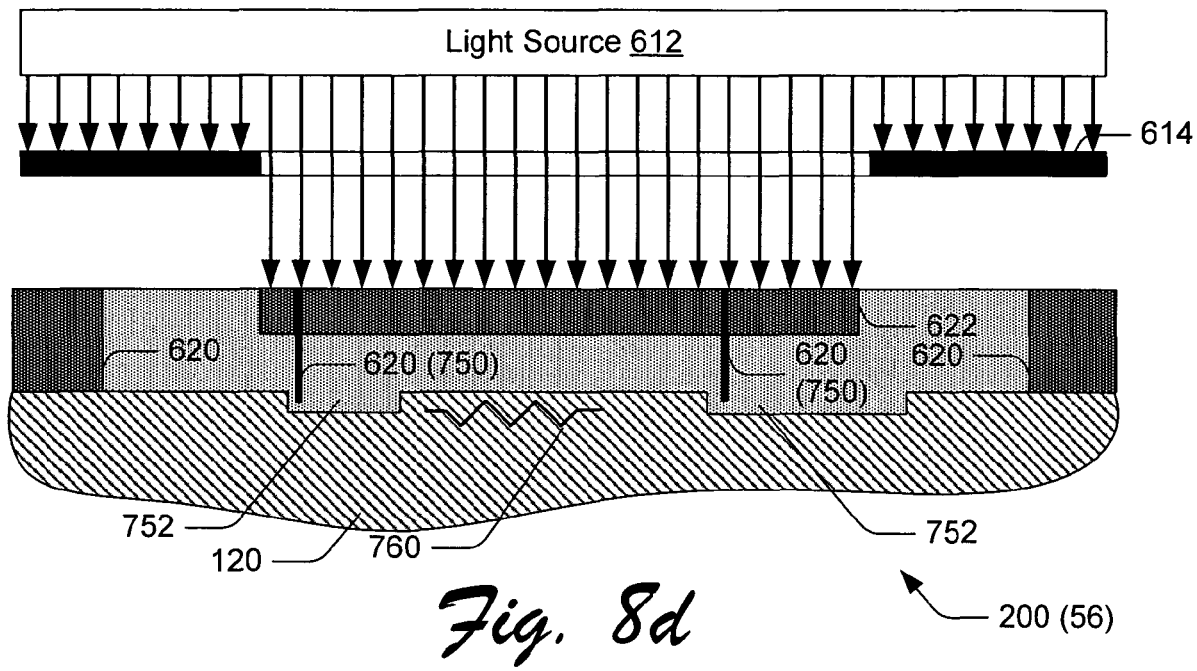
Figure 8E:
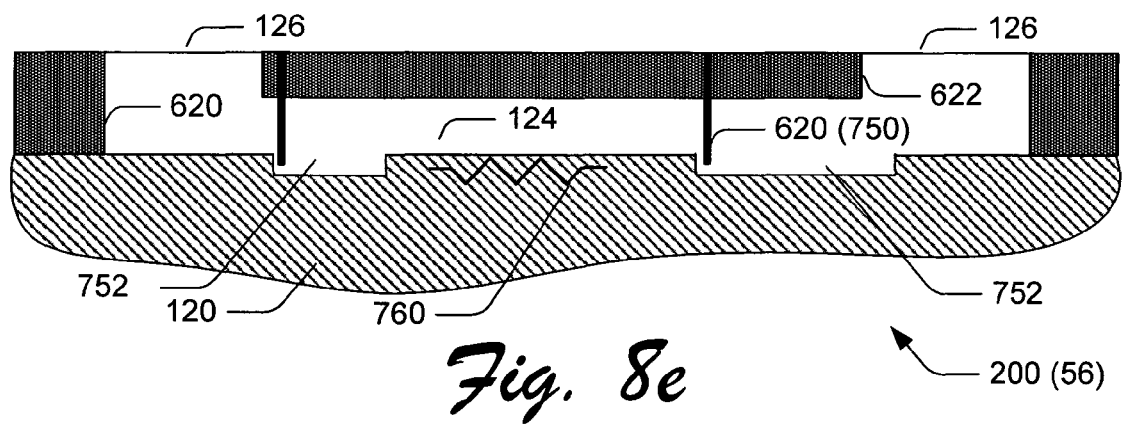
Figure 9A:
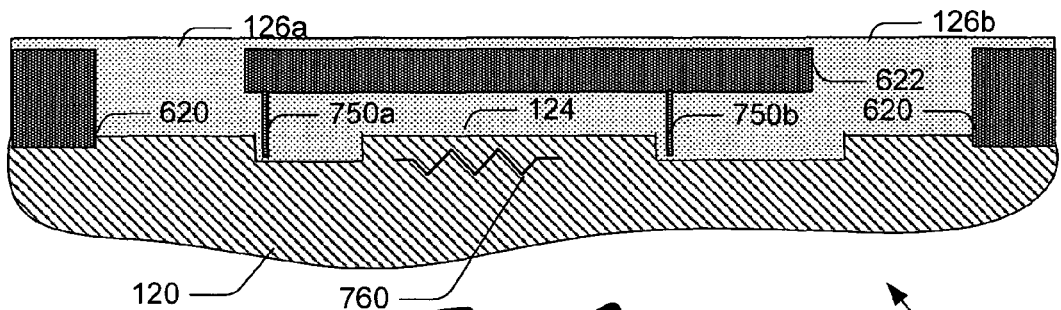
FIGS. 9a, 9b, 9c, and 9d illustrate one embodiment of the operation of the fluidic MEMS pump illustrated in FIG. 8e.
Figure 9B:
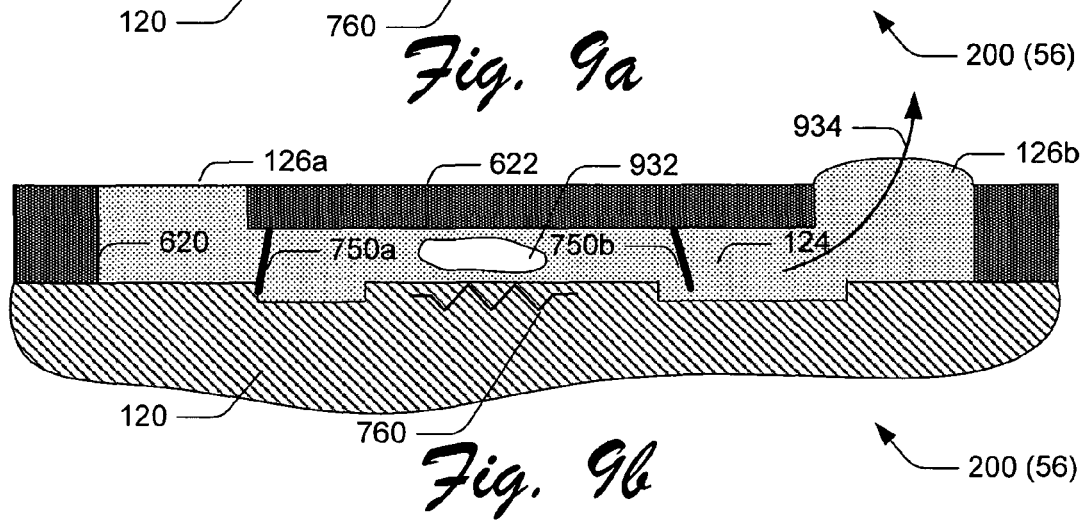
Figure 9C:
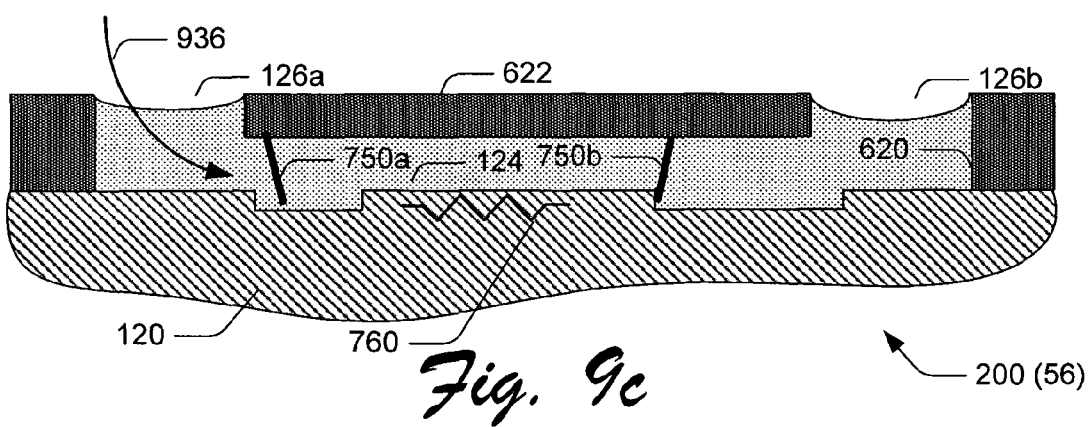

FIGS. 9a, 9b, 9c, and 9d illustrate one embodiment of the operation of the fluid pump 56 embodiment of the fluidic MEMS device 200 that was fabricated as illustrated in FIGS. 8a, 8b, 8c, 8d, and 8e. There are a plurality of micro-check valves 750 that are referenced by characters 750a and 750b for a respective input micro-check valve and an outlet micro-check valve. In general, the pairs of micro-check valves 750a and 750b in the embodiment of fluid pump 56 are in one of three positions: a) relaxed as shown in FIG. 9a; b) moved apart as shown in FIG. 9b; and c) moved together as shown in FIG. 9c.

There are a plurality of through-holes 126 that are referenced by characters 126a and 126b for a respective input through-hole and an outlet through-hole. The fluid pump 56 is configured with a fluidic channel portion 124 with which the input through-hole 126a and the outlet through-hole 126b is in fluidic communication. As with fluid pumps in general, the general purpose of the fluid pump 56 is to transport fluid from the input through-hole 126a via the fluidic channel portion 124 to the outlet through hole 126b. FIG. 9a illustrates the fluid pump at an initial (relaxed) state in which the inlet micro-check valve 750a and the outlet micro-check valve 750b are both in their relaxed state. The two micro-check valves 750 can only open one way, to the right with directions as shown in FIG. 9a.

In FIG. 9b, a bubble 932 is generated within the fluidic channel portion 124 between the inlet micro-check valve 750a and the outlet micro-check valve 750b. The bubble can be generated thermally by, in one embodiment, applying an electric current or voltage to the resistor 760. Generating the bubble 932 has the effect of increasing fluid pressure in the fluid within the fluidic channel portion 124 between the micro-check valves 750a and 750b, and therefore opens the micro-check valve 750b to the right as shown in FIG. 9b. As mentioned in this disclosure, a piezoelectric device can be used in place of the resistor to provide a pumping action within the fluid pump 56. This opening the micro-check valve 750b to the right has the effect of forcing fluid (within the fluidic channel portion 124) out of the outlet through-hole 126b in a direction as indicated by the arrow 934.

In FIG. 9c, the bubble 932 illustrated in FIG. 9b collapses. Collapsing the bubble 932 has the effect of decreasing the fluid pressure of the fluid within the fluidic channel portion 124 between the micro-check valves 750a and 750b, and therefore micro-check valve 750a opens to the right as shown in FIG. 9c. The displacement of the inlet micro-check valve 750a to the right as shown in FIG. 9c has the effect of pulling fluid into the fluidic channel portion 124 through the inlet through-hole 126a in a direction as indicated by the arrow 936.

Figure 9D:
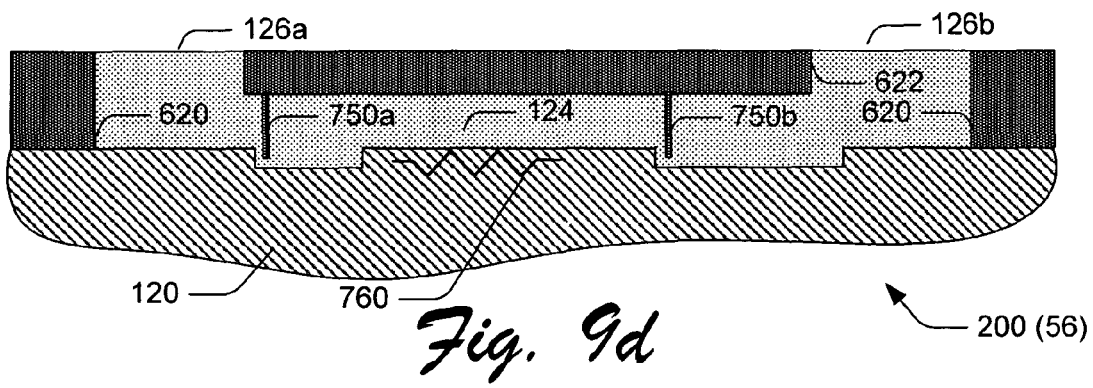

FIG. 9d shows the return of both micro-check valves 750a and 750b to their relaxed state, similar to their state as shown in FIG. 9a. When the fluid pump 56 is in its relaxed state as shown in FIG. 9d, it is positioned to start another pumping cycle as illustrated in FIGS. 9a, 9b, 9c, and 9d.

Figure 10:
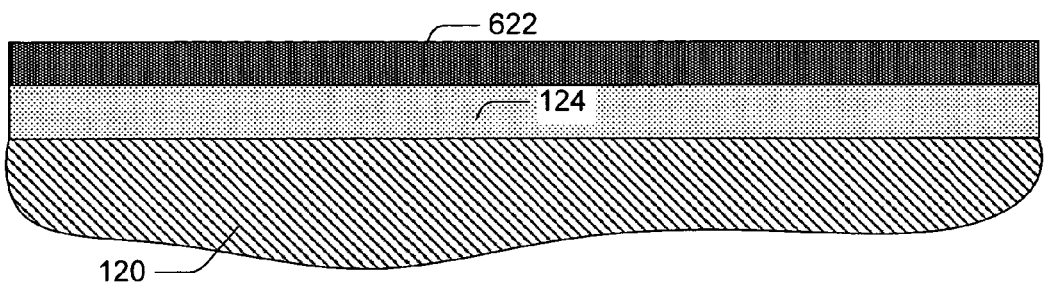
FIG. 10 illustrates a side cross sectional view of one embodiment of the fluidic MEMS device (in this instance a fluidic channel)

A variety of MEMS devices are now described that can be produced using the deep cross-linked polymer region 620 that is exposed as described relative to FIG. 8c, and the shallow cross-linked polymer region 622 that is exposed as described relative to FIG. 8d. FIG. 10 illustrates one embodiment of the fluidic MEMS device 200 that is configured as a fluidic channel portion 124 that contains no through-holes 126. Certain embodiments of the fluidic channel portion 124 with no through-holes can be used to transport fluid between pairs or sets of the fluidic MEMS devices 200. Other embodiments of the fluidic channel portion 124 with no through-holes can be used to house certain types of fluidic MEMS devices such as filters 46, micro-check valves 48, reactors 50, separators 52, waveguides 54, and pumps 56 as illustrated in FIG. 3. Unexposed polymer layer materials are developed away to form the fluid channel. With direct imaging, there are a large number of holes to leave unexposed to permit, following exposure, the unexposed materials within the fluidic channel to escape through the holes to thereby create the fluid channels. Following the direct imaging process, these holes are plugged preferably by applying a sealing glue or epoxy (that can be applied precisely using automatic machines that provide the necessary precision in drop placement and drop size.

Figure 11:
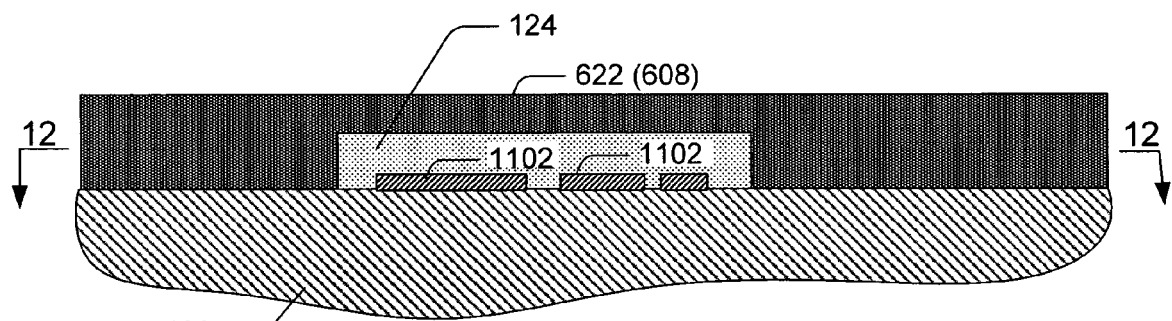
FIG. 11 illustrates a side cross sectional view of one embodiment of the fluidic MEMS device (in this instance a reactor)
Figure 12:
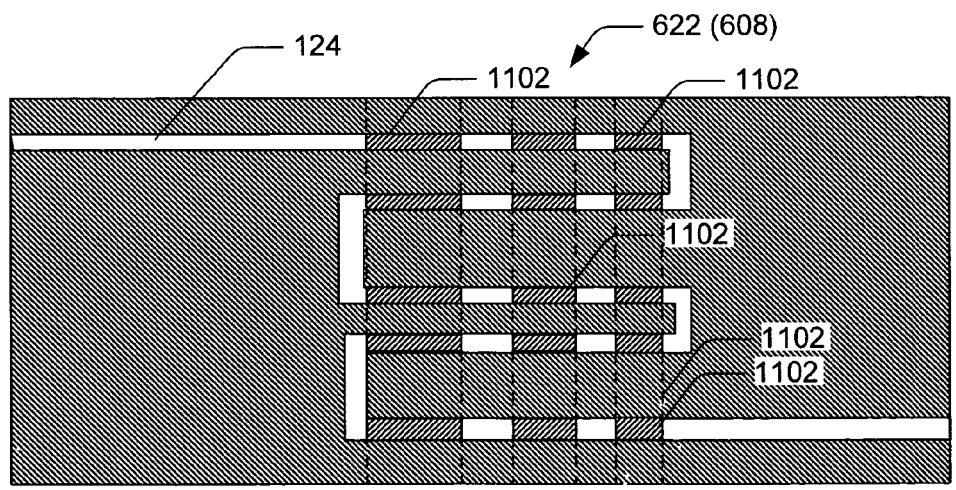
FIG. 12 illustrates a top cross sectional view of the fluidic MEMS device illustrated in FIG. 11 as taken through sectional lines 12-12.

FIGS. 11 and 12 illustrate a respective side cross-sectional and top cross-sectional embodiment of the fluidic MEMS device 200 that can be fabricated using the direct imaging process 700, one embodiment of which is described relative to FIG. 7. The FIGS. 11 and 12 embodiments of the fluidic MEMS device 200 is a reactor 50 as illustrated in FIG. 3. The reactor 50 acts to heat the fluid passing through to different levels by selectively heating multiple heating elements through different temperatures as per the polymerase chain reaction (PCR) process or other similar process that uses a reactor. To provide the heat, a plurality of heating elements 1102 are attached to the substrate 120 in close proximity to the fluidic channel portion 124. Each heating element 1102 can have different areas, be applied different distances from the fluid conduit, or have controllable electric current applied thereto, to alter the temperature of the fluid traversing the fluid channels to different levels. The heating element can be attached to the substrate as a portion of 701 of the embodiment of direct imaging process 700 as shown in FIG. 7 (i.e., prior to the deposition of the polymer layer 608 on the substrate as illustrated in FIG. 6b). The particular configuration of the heating element is a design choice.

Figure 13:
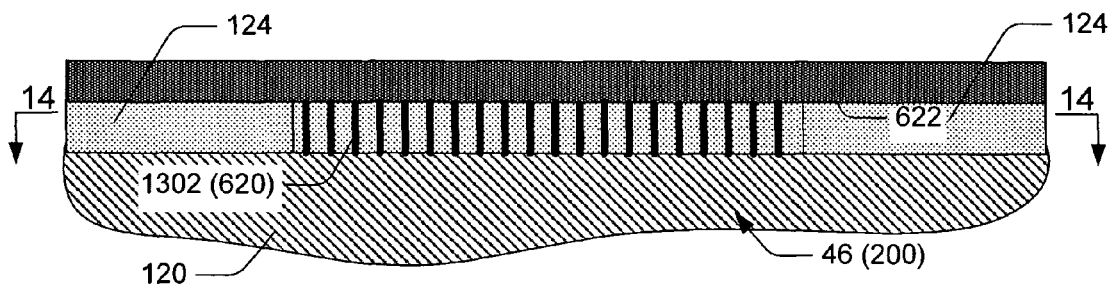
FIG. 13 illustrates a side cross sectional view of one embodiment of the fluidic MEMS device (in this instance a filter)
Figure 14:
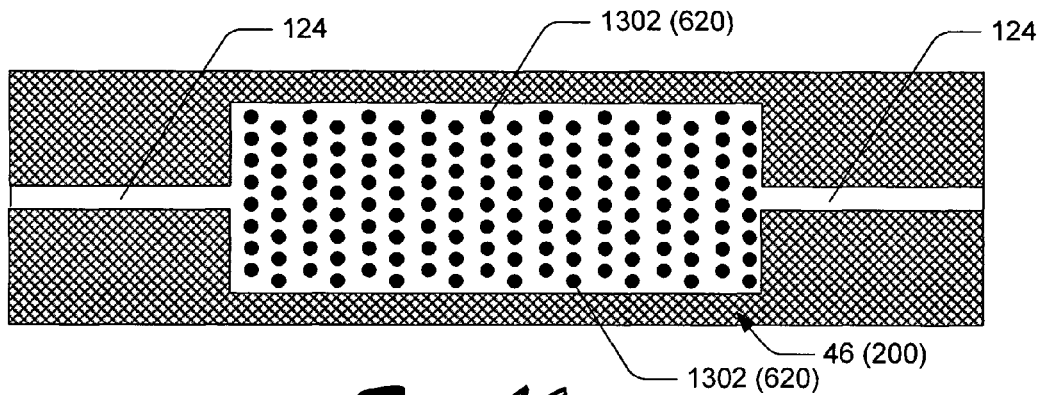
FIG. 14 illustrates a top cross sectional view of the fluidic MEMS device illustrated in FIG. 13 as taken through sectional lines 14-14.

FIGS. 13 and 14 show respectively a side cross-sectional view and a top cross-sectional view of another embodiment of the fluidic MEMS device 200. The embodiment of fluidic MEMS device shown in FIGS. 13 and 14 is a filter 46 as illustrated in FIG. 3. The filter 46 can be fabricated using the direct imaging process 700 as shown in FIG. 7. The filter 46 includes a plurality of filter elements 1302 that are spaced at a prescribed distance from each other to provide a desired filtering function for objects contained within the fluid passing through the filter 46 that are greater than a prescribed dimension. The filter elements 1302 are secured to the substrate by exposing each fluid element for a sufficient duration to cross-link the polymer in that filter element through the entire height of the fluid channel.

The filter elements 1302 can be fabricated as one embodiment of deep cross-linked polymer regions 620 as described relative to FIGS. 6c and 8c. With reference to FIG. 8c, the lower-most portion of the micro-check valves 750 (another embodiment of deep cross-linked polymer regions 620) are not secured to the substrate, while the filter elements 1302 are secured at their lowest point to the substrate. Whether the deep cross-linked polymer regions 620 is secured at its lowest point to the substrate 120 is a design choice, and can be determined based on the different materials, configurations and fasteners applied between the particular deep cross-linked polymer region 620 and the substrate.

Figure 15:
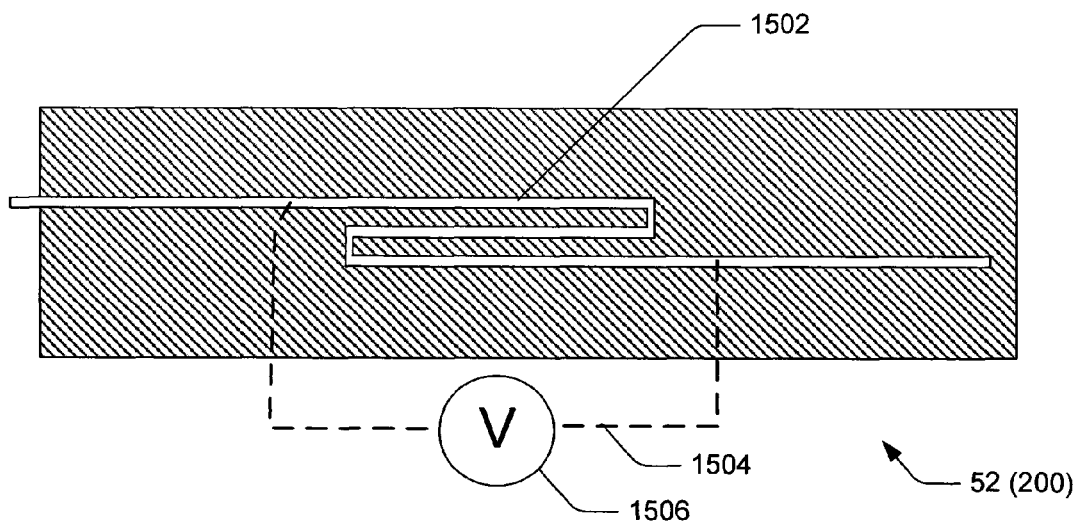
FIG. 15 illustrates a side cross sectional view of one embodiment of the fluidic MEMS device (in this instance a separator)

Another embodiment of the fluidic MEMS device 200 shown in FIG. 15 is configured as the separator 52 (described relative to FIG. 3). The separator 52 includes a fluidic channel 1502 that is formed similarly to the fluidic channel portion 124 that is described relative to FIG. 10. The fluidic embodiment of the channel portion 1502 shown in FIG. 15 is configured as a serpentine to provide a greater channel length that of the fluidic channel. Increasing the length of the fluidic channel will increase the length through which the fluid traversing the fluidic channel may be separated, and thereby improve the separation. Any configuration of channel, however, is within the intended scope of the present disclosure. A voltage source 1506 is applied via electrical conductors 1504 to different portions of the channel portion 1502. The electrical charge being applied to the different portions of the channel portions acts to create an electrical field within the electric fluid passing through the channel portions (that can separate material within the fluid that passing through the channel portion based on electrophoresis). In one embodiment, voltage from the voltage source is applied across the inlet and outlet to provide potential so that the charged particles can be moved from inlet to outlet. In one embodiment, the channel portion 1502 and the electrical conductors 1504 (and also possible the voltage source 1506) are integrated within the polymer layer relative to the substrate during 701 in the direct imaging process 700 shown in FIG. 7. The separator 52 as shown in FIG. 15 functions by electrophoresis, in which the electric voltage applied to the electrical conductor path 1502 acts to separate particles that are flowing through the separator based on their electrical charge.

Figure 16:
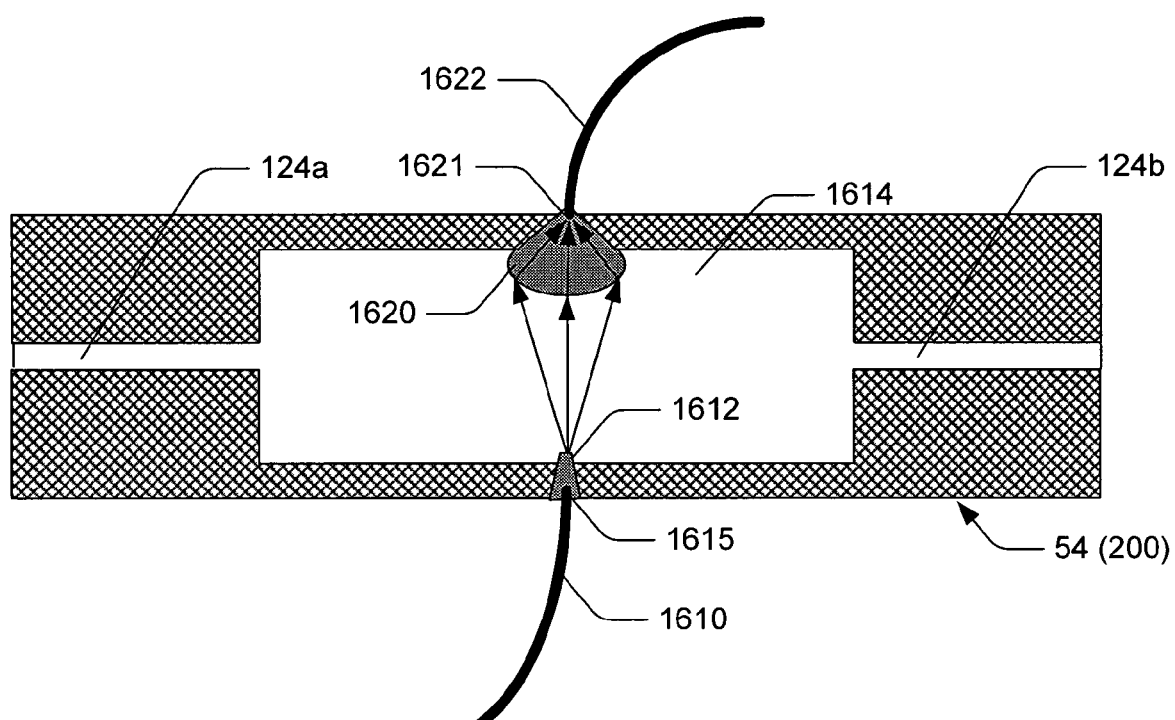
FIG. 16 illustrates a side cross sectional view of one embodiment of the fluidic MEMS device (in this instance an optical waveguide)

Another embodiment of the fluidic MEMS device 200 that is shown in FIG. 16 is configured as the optical waveguide 54 as shown in the FIG. 3 block diagram. The optical waveguide 54 includes an input optical conduit 1610 that inputs light into a detector region 1614 from a light source 1612. Light is directed from the light source 1612 across the fluid detection region 1614 towards a focusing lens 1620. As indicated by the optical waveguide, certain embodiments of the fluidic MEMS device 200 can be configured with an optical portion. Light that is received at the focusing lens 1620 is directed into an output optical conduit 1622. Both conduits 1610 and 1622 may be optical fibers in one embodiment of the optical waveguide 54. Fluid that is to undergo chemical and/or biological analysis is input into the input fluidic channels 124a, and traverses the fluid detection region 1614 to exit into the outlet fluidic channel 124b. Respective light source 1612 and focusing lens 1620 are provided with respective guides or slots 1615 and 1621 to maintain respective optical conduits 1610 and 1622 in their respective secured and optically-coupled positions. The optical waveguide 54 therefore can be used to transmit a signal to an external optical detector which detects optical characteristics of any fluid that can be passed through the fluid detection region 1614.

One aspect of the optical waveguide 54 embodiment of the fluidic MEMS device 200 is that it applies to an optical device. As such, an optical portion can be provided in the fluidic MEMS device 200 to perform any optical function that is desired. It is envisioned that the optical waveguide 54 can be configured using a deep cross-linked polymer region 620 as described relative to FIG. 6c in the direct imaging process 700 shown in FIG. 7.

Light could be introduced from the light source 1612 across the entire vertical height of the fluid detection region 1614, in which case the focusing lens 1620 should also extend across the entire vertical height of the fluid detection region 1614 (and the focusing lens 1620 configured as a deep cross-linked polymer region 620 device). The focusing lens 1620 can be fabricated as a shallow cross-linked polymer region 622 device.

It is also possible to fabricate optical couplers using the direct imaging process 700 as shown in FIG. 7. There are a considerable variety of configurations of focusing lens that can be applied to waveguides while remaining within the concepts of the present disclosure.

Certain structural aspects of the through-hole 126 have been described relative to FIGS. 4 and 5. Another embodiment of the through-hole 126 is described relative to FIGS. 17 and 18 that illustrate, respectively, a top cross-sectional view and a side cross sectional view. The through-hole 126 can be fabricated on the substrate 120 by using a combination of deep cross-linked polymer regions 620 and shallow cross-linked polymer regions 622. A connector portion 2002 is shown as being connected to the thru-hole 126 in the embodiments of FIGS. 17 and 18. The connector portion 2002 includes a tubule recess 2003 through which fluids can be applied via the through-hole 126 to or from the fluidic channel 124. In one embodiment, the deep cross-linked polymer regions 620 provide support for the through-hole 126 and define the lateral boundaries of any fluidic channel 124 that is in fluidic communication with the through-hole 126. The shallow cross-linked polymer region 622 provides the polymer configuration that immediately surrounds the opening of the through-hole 126.

In one embodiment, the connector portion 2002 is securely attached to a mounting about the through-hole 126 using glue 2010. This disclosure thereby provides a mechanism by which the top-hat structure (many horizontally extending cross-linked polymer regions adjacent and partially defining through-holes 126) act as an anchor 1902 to provide a more solid mounting for glues, cements, or epoxies to attach. The through-holes having a built-in anchor 1902 to provide a more secure mounting for glues allows the glues to form a better seal of the through-holes and secures the connector portions 2002 more positively to the through-hole. The glue 2010 allows for maintaining the connector portion 2002 sealed in a position in which fluids can be applied via the tubule recess 2003 through the thru-hole to or from the fluidic channel 124. The glue can be an epoxy that helps to seal to form an anchor 1902 that when pulled will not separate. In another embodiment, some mechanical fastener or other mechanism can be used to secure the fluid coupling fitting 2002 relative to the substrate within the through-hole 126.

Figure 17:
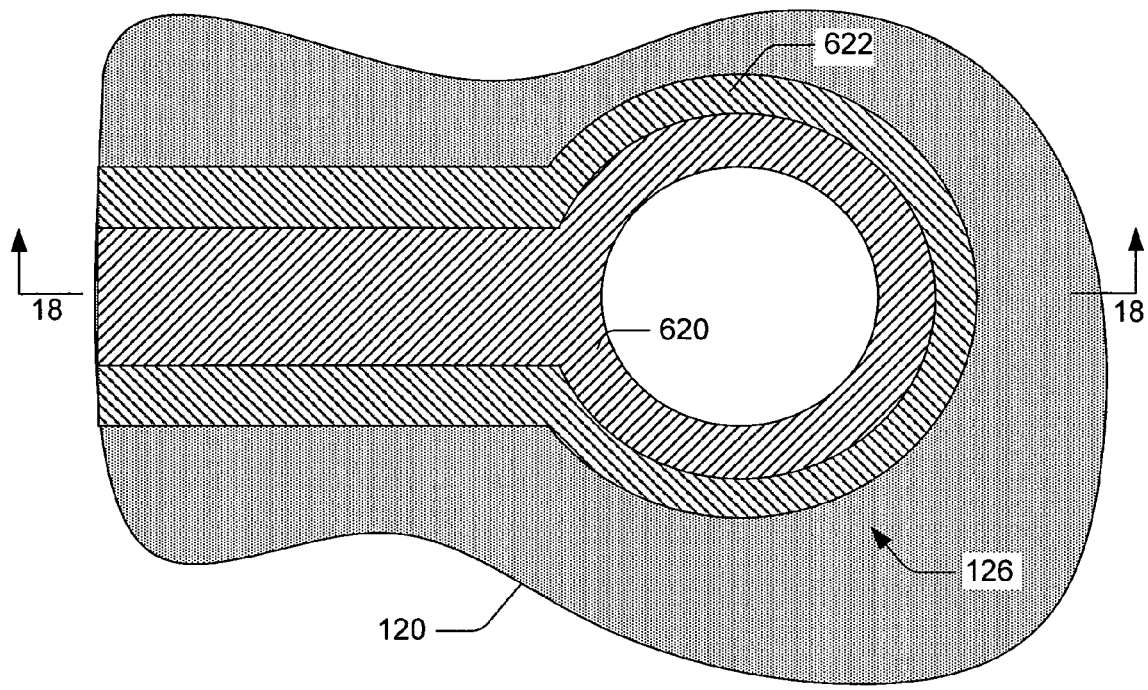
FIG. 17 illustrates a top view of one embodiment of a through-hole.
Figure 18:
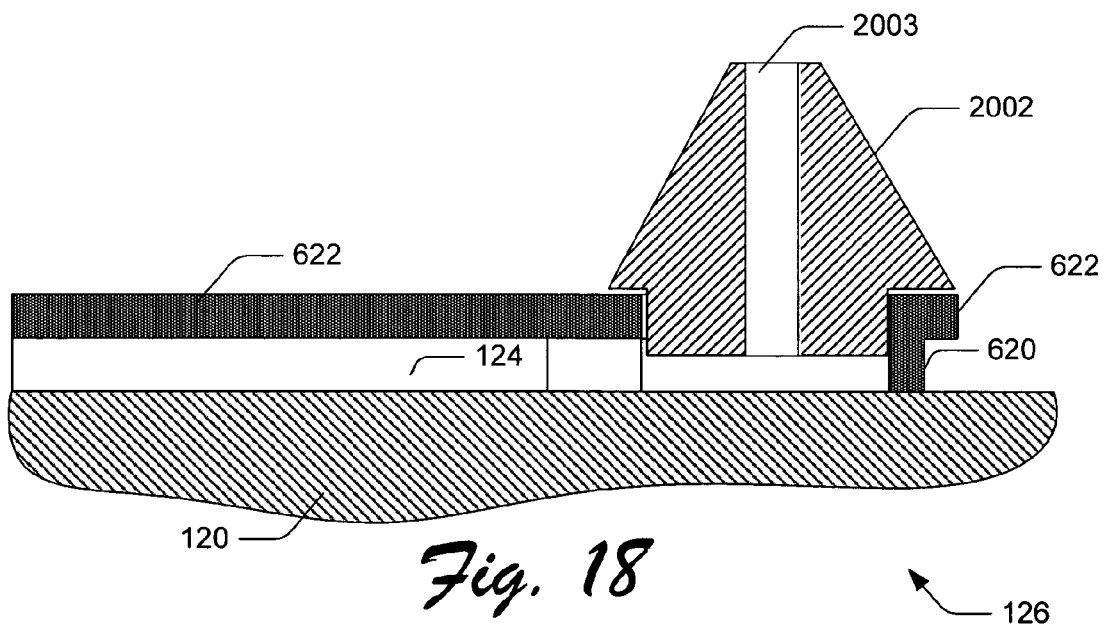
FIG. 18 illustrates a side view of one embodiment of the through-hole illustrated in FIG. 17 as taken through sectional lines 18-18 in FIG. 17.
Figure 19:
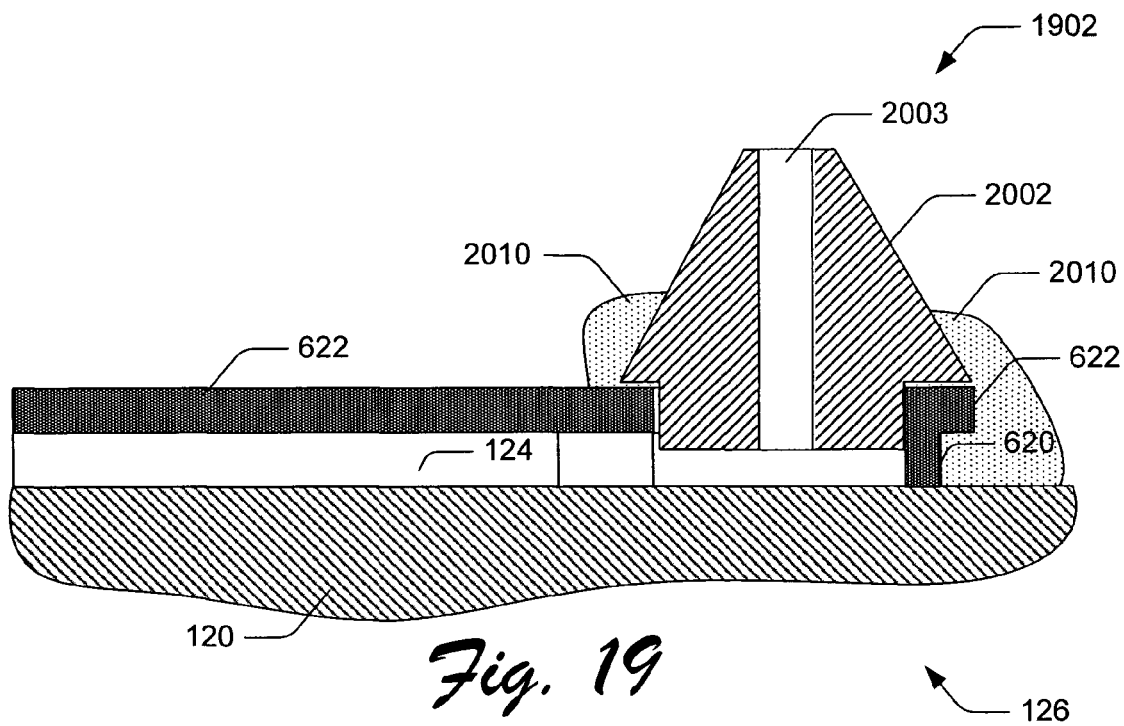
FIG. 19 illustrates the through-hole of FIG. 18 with glue maintaining the conduit components connected.
Figure 20:
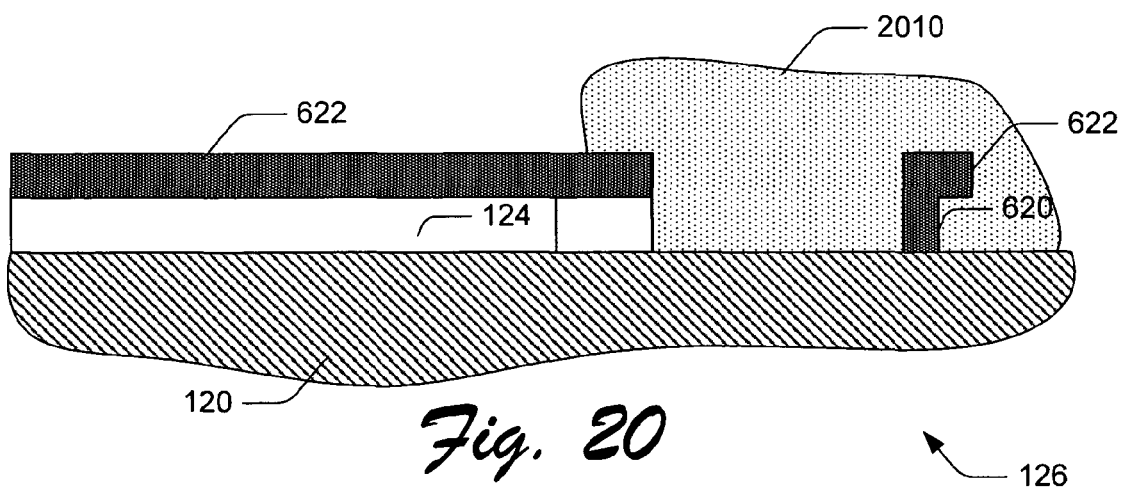
FIG. 20 illustrates the through-hole of FIG. 18 with a conduit portion removed, and glue provided to seal off the pass-thru.

The embodiment of through-hole 126 as shown in FIGS. 17 and 18 can be sealed when the connector portion 2002 is removed from the through-hole 126. As shown in FIG. 20, the glue 2010 such as an epoxy is applied to the through-hole 126 with no connector portion 2002 as shown in FIG. 18 is present to form the seal. The glue or epoxy seals against fluid passing though the through-hole.

While the embodiments described above describe a direct imaging embodiment that can be used to create a variety of fluidic MEMS devices 200, it is also envisioned that other processes can be used to create fluidic MEMS devices 200 and are also within the scope of the present disclosure. One of these processes is referred to as the "Lost Wax" process, and another one of these processes is referred to as a "Dry Film" process to create a fluidic MEMS device 200. These two processes are now described.

Figure 21A:
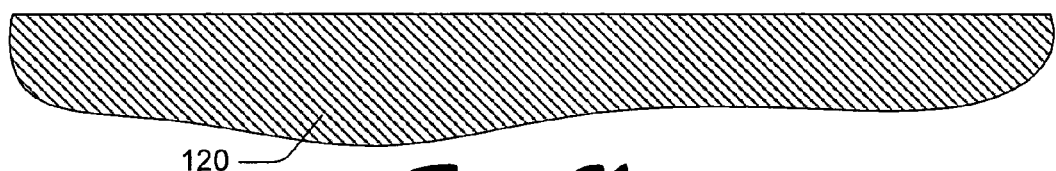
FIGS. 21a, 21b, 21c, 21d, and 21e illustrate one embodiment of a so-called "lost wax" process.
Figure 21B:
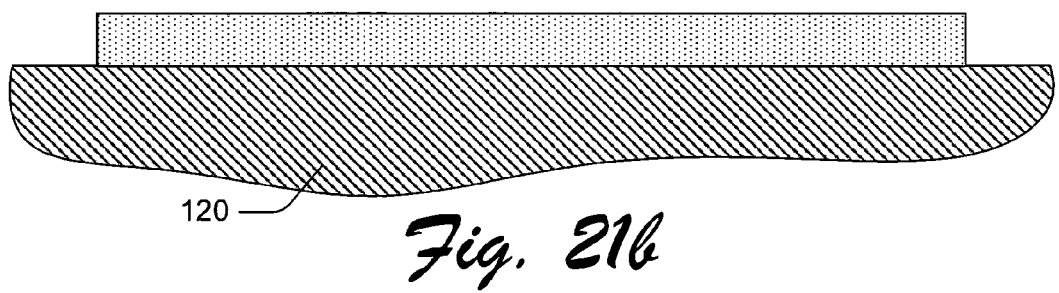
Figure 21C:
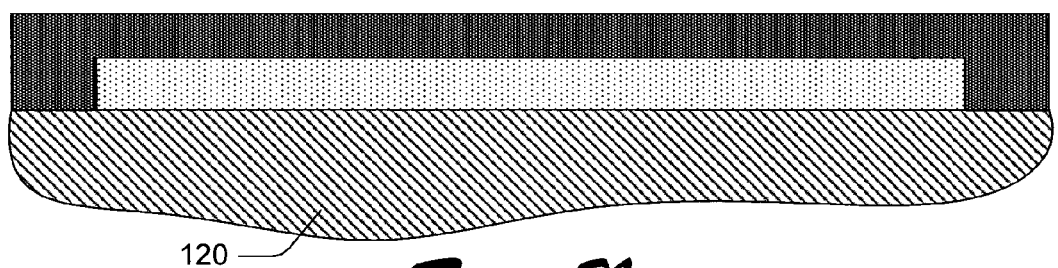
Figure 21D:
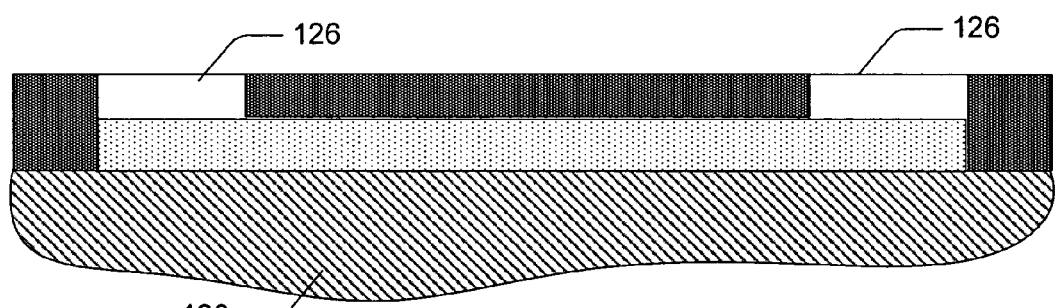
Figure 21E:
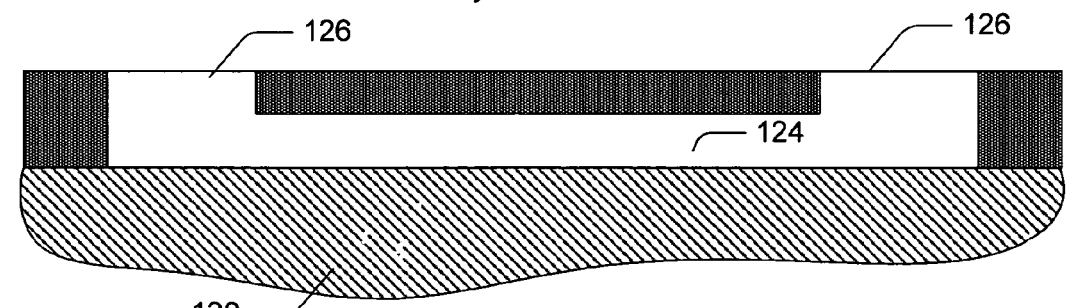
Figure 22:
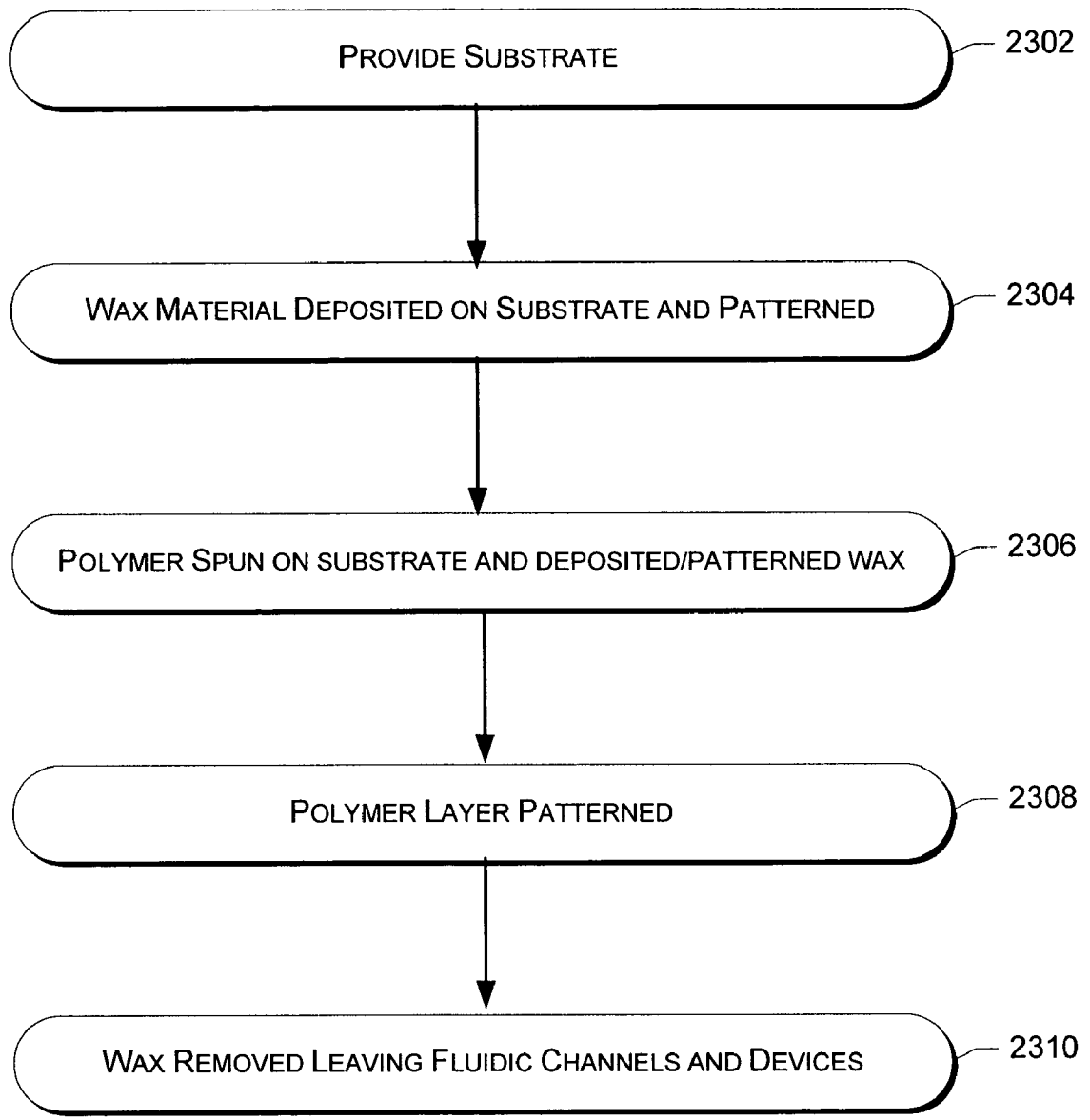
FIG. 22 illustrates a flow chart of the embodiment of the lost wax process shown in FIGS. 21a, 21b, 21c, 21d, and 21e.

FIGS. 21a, 21b, 21c, 21d, and 21e illustrated one embodiment of the lost wax process that is described in combination with a flow chart describing the lost wax process 2300 as shown in FIG. 22. In FIG. 21a, a substrate 120 is provided upon which the fluidic MEMS device 200 is to be constructed as described in 2302 in FIG. 22. In FIG. 21b, a sacrificial material 2204 (such as a photoresist) is deposited on the substrate 120 as described in 2304 in FIG. 22. The pattern of the sacrificial material generally corresponds to the pattern of the fluidic channels. Other more complex shapes (e.g., filter elements for a fluidic filter and microcheck valves for a fluidic pump) can be formed by creating inverse patterns and/or shapes in the sacrificial material.

In FIG. 21c, a polymer 2206 is spun on the substrate 120 over the sacrificial material 2204 as described in 2306 in FIG. 22. The polymer forms a polymer layer that in combination with the substrate encloses the fluidic MEMS channel. The polymer 2206 is therefore a unitary member, and is formed using a single deposition process.

In FIG. 21d, the polymer 2206 is patterned (portions are removed) using known polymer patterning techniques as described in 2308 in FIG. 22. The pattern can be used to form thru-holes 126 through which fluid can pass in the fluidic MEMS device 200 as described above. Alternatively, the pattern can be used to form release holes through which the sacrificial material is removed.

In FIG. 21e, the sacrificial material (such as photoresist) is developed away and then removed using the so-called "lost wax" technique as described relative to 2310 in FIG. 22. In one aspect, the sacrificial material is developed away using a developer's solution, and the sacrificial material is then removed through the thru-holes, with dry or wet etch. The voids left by the sacrificial material are used to define the fluidic channels. As indicated in FIG. 21e, the resulting fluidic MEMS device 200 created using the lost wax technique is similar to the fluidic MEMS device 200 produced using direct imaging techniques as described above. A plurality (even a large number) of related and/or unrelated fluidic MEMS devices 200 can be fabricated simultaneously using the lost wax process described relative to FIGS. 21a, 21b, 21c, 21d, and 21e.

Figure 23A:
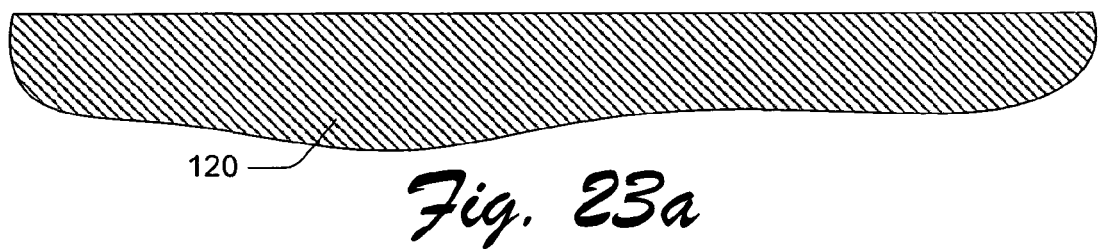
FIGS. 23a, 23b, 23c, and 23d illustrate one embodiment of a dry film process.
Figure 23B:
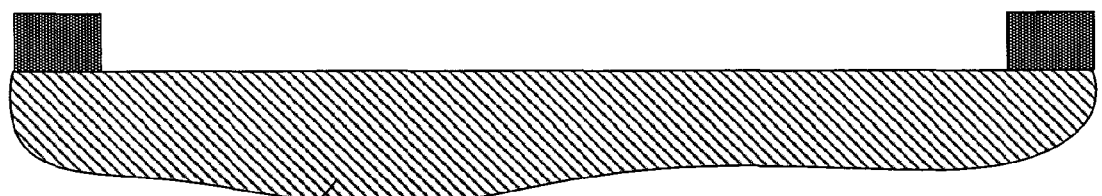
Figure 23C:
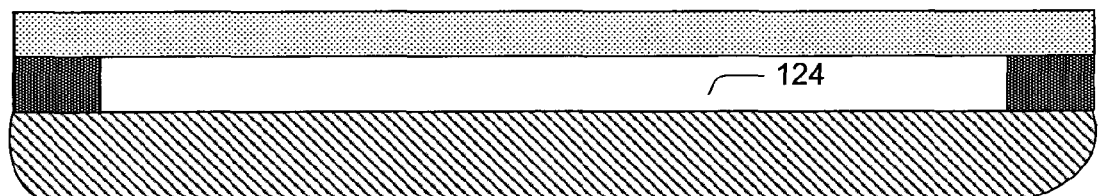
Figure 23D:
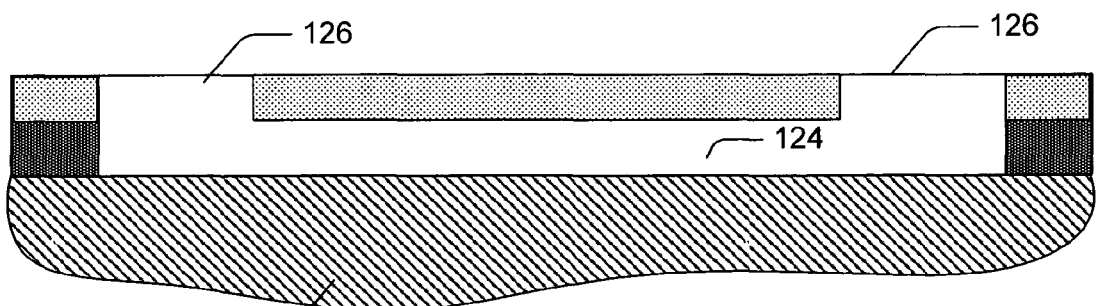
Figure 24:
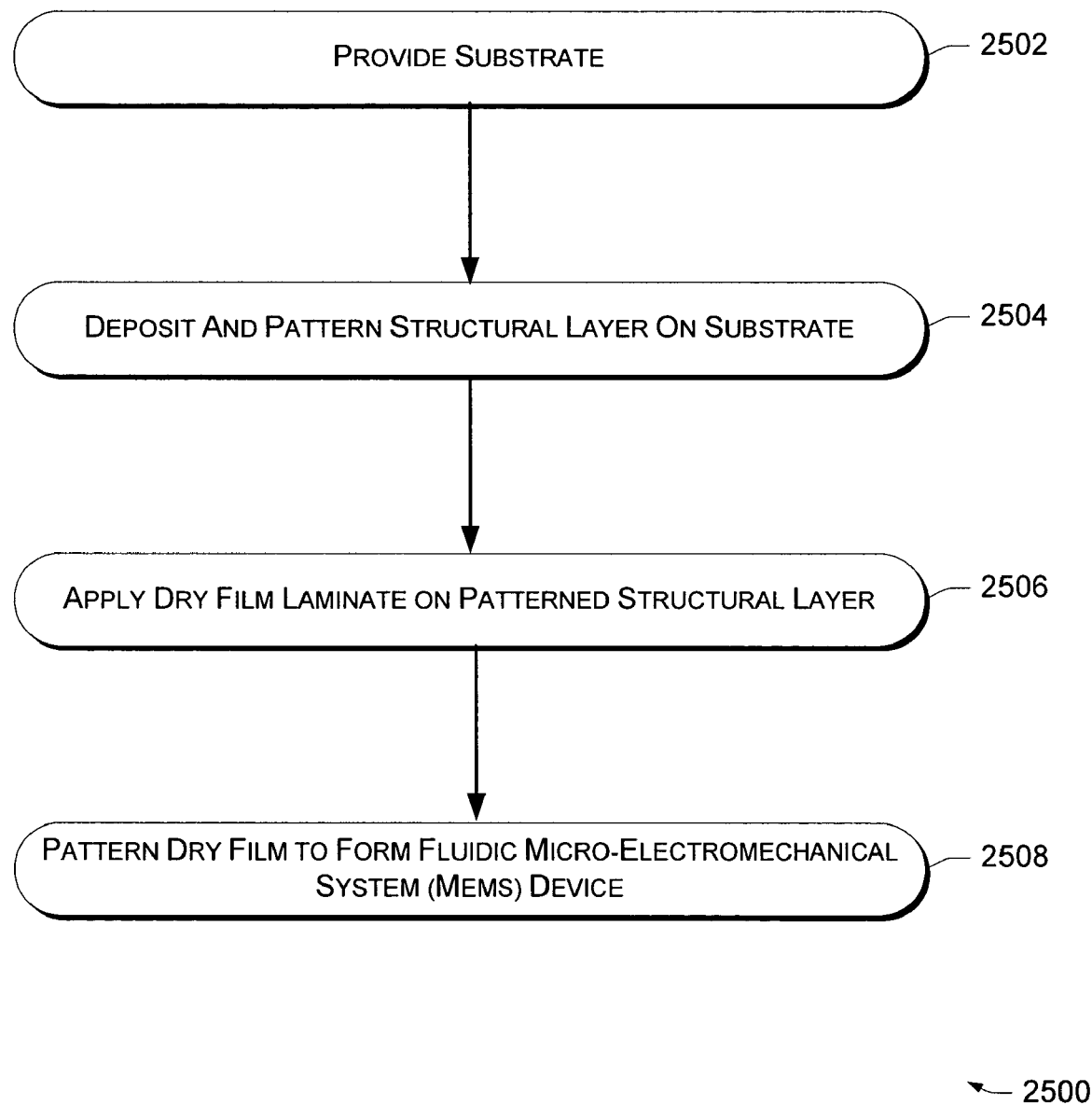
FIG. 24 illustrates a flow chart of the embodiment of the dry film process shown in FIGS. 23a, 23b, 23c, and 23d.

FIGS. 23a, 23b, 23c, and 23d illustrated one embodiment of the dry film process that is described in combination with a flow chart describing the dry film process 2500 as shown in FIG. 24. In FIG. 23a, a substrate 120 is provided upon which the fluidic MEMS device 200 is to be constructed as described in 2502 of the dry film process 2500 in FIG. 24. In FIG. 23b, a structural polymer layer and patterning 2404 is deposited on the substrate using known polymer deposition and patterning techniques as described in 2504 in FIG. 24. The contour of the structural polymer layer and patterning 2404 are configured to partially surround and partially enclose the fluidic channel of the fluidic MEMS device 200 that is subsequently formed using the dry film process.

FIG. 23c shown the application of a dry film lamination layer 2406 that is deposited on top of, and seals with, the structural polymer layer and patterning 2404 as described relative to 2506 in FIG. 24. The fluidic channel of the fluidic MEMS device 200 is therefore created within the substrate 120, the structural polymer layer and patterning 2404, and the dry film lamination layer 2406. More complex shapes and patterns to form the different types of the fluidic MEMS device 200 can be provided by patterning of one of these three members 120, 2404, or 2406; or alternatively by securing additional components to one or more of these three members 120, 2404, or 2406.

FIG. 23d shows the patterning of the dry film lamination layer 2406 to create the desired fluidic MEMS device(s) 200 as described relative to 2508 in FIG. 24. The patterning of the thru-holes 126 and other portions of the fluidic MEMS device 200 can be provided during this patterning. A plurality (even a large number) of related and/or unrelated fluidic MEMS devices 200 can be fabricated simultaneously using the dry film technique described relative to FIGS. 23a, 23b, 23c, and 23d.

Figure 25:
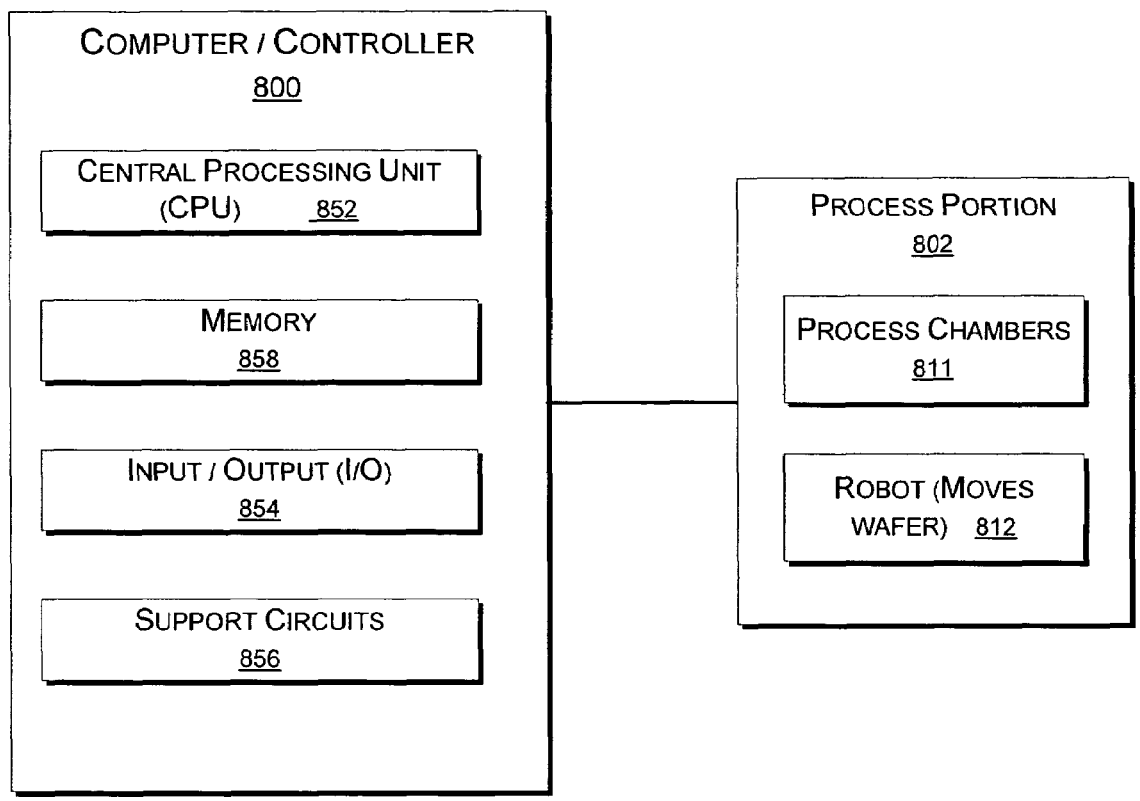
FIG. 25 illustrates a block diagram of one embodiment of a computer/controller that is configured to control the direct imaging process such as illustrated in FIG. 7.

FIG. 25 illustrates one embodiment of a controller or a computer 800 that controls the direct imaging process 700. A process portion or "fab" is illustrated as 802. The process portion 802 may include a variety of process chambers 811 that the wafer 306 is translated between (often using a robot mechanism 812) such as indicated in the direct imaging process 700 of FIG. 7. The particulars of the direct imaging process 700 vary with the materials that are deposited and then etched. The processing of different polymers often varies between different suppliers and different configurations. Such processes as chemical vapor deposition, physical vapor deposition, and electrochemical deposition can be applied within the process portion 802.

The controller or the computer 800 comprises a central processing unit (CPU) 852, a memory 858, support circuits 856 and input/output (I/O) circuits 854. The CPU 852 is a general purpose computer which, when programmed by executing software 859 contained in memory 858, becomes a specific purpose computer for controlling the hardware components of the processing portion 802. The memory 858 may comprise read only memory, random access memory, removable storage, a hard disk drive, or any form of digital memory device. The I/O circuits comprise well known displays for output of information and keyboards, mouse, track ball, or input of information that can allow for programming of the controller or computer 800 to determine the processes performed by the process portion 802 (including the associated robot action included in the process portion). The support circuits 856 are well known in the art and include circuits such as cache, clocks, power supplies, and the like.

The memory 858 contains control software that when executed by the CPU 852 enables the controller or the computer 800 that digitally controls the various components of the direct imaging process 700 as shown in FIG. 7. In another embodiment, the computer or controller 800 can be analog. For instance, application specific integrated circuits are capable of controlling processes such as occur within the process portion 802.

Although the invention is described in language specific to structural features and methodological steps, it is to be understood that the invention defined in the appended claims is not necessarily limited to the specific features or steps described. Rather, the specific features and steps disclosed represents preferred forms of implementing the claimed invention.

The invention claimed is:

1. An apparatus, comprising:
   a fluidic Micro Electro-Mechanical System (MEMS) comprising a polymer layer joined to a substrate portion, the polymer layer of the apparatus comprising:
      a containment portion that in combination with the substrate defines a fluidic channel, wherein the containment portion includes a deep cross-linked polymer region and a shallow cross-linked polymer region, and
      wherein the deep cross-linked polymer region and the shallow cross-linked polymer region of the containment portion are formed as a unitary structure.

2. The apparatus of claim 1, further comprising a resistor located in, on, or adjacent to the substrate.

3. The apparatus of claim 1, wherein a portion of the containment portion that does not contact the substrate includes a shallow cross-linked polymer region and a portion of the containment portion that contacts the substrate includes a deep cross-linked polymer region.

4. The apparatus of claim 3, wherein portions of the containment portion that includes the shallow cross-linked polymer region are on lateral sides of the fluidic channel.

5. The apparatus of claim 3, wherein portions of the containment portion that includes the deep cross-linked polymer region are separated by the fluidic channel from the substrate.

6. The apparatus of claim 1, wherein the apparatus acts as a pump.

7. The apparatus of claim 1, wherein the apparatus acts as a polymerase chain reaction (PCR) reactor.

8. The apparatus of claim 1, wherein the apparatus acts as a separator.

9. The apparatus of claim 1, wherein the apparatus acts as an optical waveguide.

10. The apparatus of claim 1, wherein the apparatus acts as a filter.

11. The apparatus of claim 1, wherein the deep cross-linked polymer region and the shallow cross-linked polymer region are produced using direct imaging techniques.

12. The apparatus of claim 1, wherein the deep cross-linked polymer region and the shallow cross-linked polymer region are produced using lost wax techniques.

13. The apparatus of claim 1, wherein the deep cross-linked polymer region and the shallow cross-linked polymer region are produced using dry film techniques.

* * * * *